United States Patent
Morris et al.

(10) Patent No.: US 11,254,662 B2
(45) Date of Patent: *Feb. 22, 2022

(54) 2'-HALOGENATED-4'-THIO-2'-DEOXY-5-AZACYTIDINE ANALOGS AND USE THEREOF

(71) Applicant: The USA, as represented by the Secretary, Department of Health and Human Services, Bethesda, MD (US)

(72) Inventors: Joel Morris, Rockville, MD (US); Donn G. Wishka, Middletown, MD (US); Omar Diego Lopez, Walkersville, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/343,350

(22) Filed: Jun. 9, 2021

(65) Prior Publication Data

US 2021/0292310 A1 Sep. 23, 2021

Related U.S. Application Data

(63) Continuation of application No. 17/278,625, filed as application No. PCT/US2019/052410 on Sep. 23, 2019.

(60) Provisional application No. 62/736,246, filed on Sep. 25, 2018.

(51) Int. Cl.
*C07D 409/04* (2006.01)

(52) U.S. Cl.
CPC .................................. *C07D 409/04* (2013.01)

(58) Field of Classification Search
CPC .................................................. C07D 409/04
See application file for complete search history.

(56) References Cited

U.S. PATENT DOCUMENTS

| 9,884,882 B2 | 2/2018 | Ito et al. |
| 2015/0011499 A1 | 1/2015 | Baba et al. |
| 2020/0361977 A1 | 11/2020 | Zhang et al. |

FOREIGN PATENT DOCUMENTS

WO WO 2015/125781 A1 8/2015

OTHER PUBLICATIONS

US 9,187,514 B2, 11/2015, Nakamura et al. (withdrawn)
Purser et al., Fluorine in Medicinal Chemistry, 37(2) Chem. Soc. Rev. 320-330. (Year: 2008).*
Boyd et al., "Some practical considerations and applications of the National Cancer Institute in vitro anticancer drug discovery screen," *Drug development research*, 34 (2): 91-109 (Feb. 1995).
Bozhok, et al., "Synthesis, hydrolytic stability, and antileukemic activity of azacytidine nucleoside analogs," *Pharmaceutical Chemistry Journal*, 49(12): 804-809 (Apr. 4, 2016).
Daifuku et al.,. "5-aza-2', 2'-difluoro deoxycytidine (NUC013): a novel nucleoside Dna methyl transferase inhibitor and ribonucleotide reductase inhibitor for the treatment of cancer," *Pharmaceuticals*, 10(3), 14 pages. (Jul. 20, 2017).
International Search Report and Written Opinion, dated Nov. 25, 2019, issued in corresponding International Application No. PCT/US2019/052410, 13 pages.
Shoemaker, "The NCI60 human tumour cell line anticancer drug screen," *Nature Reviews Cancer*, 6(10): 813-823 (Oct. 1, 2006).
Thottassery et al., "Novel DNA methyltransferase-1 (DNMT1) depleting anticancer nucleosides, 4'-thio-2'-deoxycytidine and 5-aza-4'-thio-2'-deoxycytidine," *Cancer chemotherapy and pharmacology*, 74(2): 291-302 (Jun. 8, 2014).
Tiwari et al., "Synthesis and anti-cancer activity of some novel 5-azacytosine nucleosides," *Nucleosides, Nucleotides and Nucleic Acids*, 22 (12): 2161-2170 (Dec. 19, 2011).

\* cited by examiner

*Primary Examiner* — Patricia L Morris
(74) *Attorney, Agent, or Firm* — Klarquist Sparkman, LLP

(57) ABSTRACT

Halogenated analogs of 5-aza-2'-deoxycytidine, such as halogenated analogs of 5-aza-4'-thio-2'-deoxycytidine (5-aza-T-dCyd) are described. Pharmaceutical compositions including a halogenated analog and methods of using the halogenated analogs to inhibit neoplasia are described. In some examples, the halogenated analogs have a structure according to formula Ia, or a stereoisomer, tautomer, or pharmaceutically acceptable salt thereof:

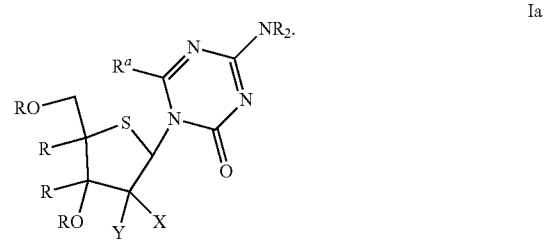

Ia

2 Claims, 29 Drawing Sheets

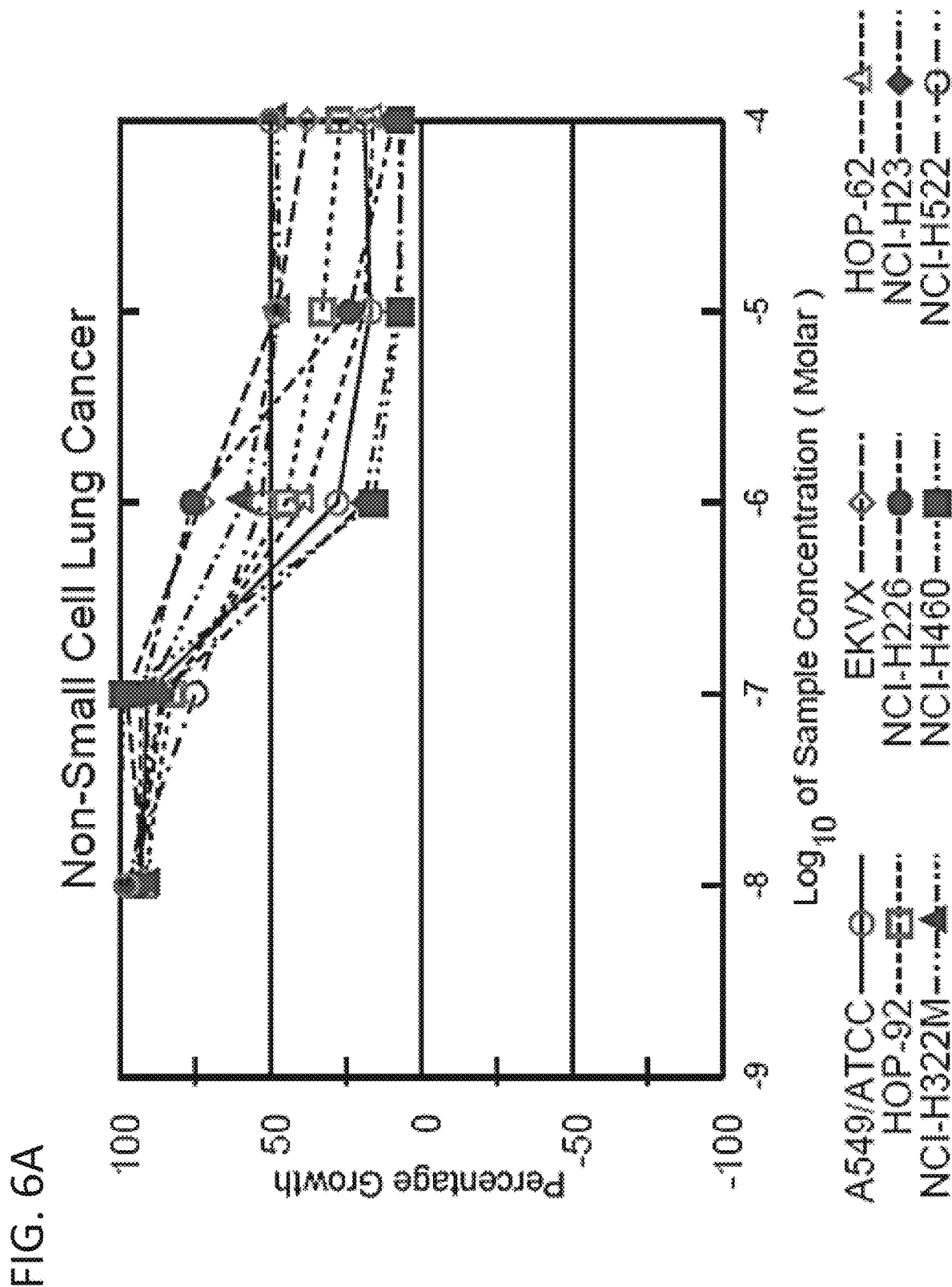

2'-HALOGENATED-4'-THIO-2'-DEOXY-5-AZACYTIDINE ANALOGS AND USE THEREOF

CROSS-REFERENCE TO RELATED APPLICATIONS

This application is a continuation of U.S. application Ser. No. 17/278,625, filed Mar. 22, 2021, which is the U.S. National Stage of International Application No. PCT/US2019/052410, filed Sep. 23, 2019, which was published in English under PCT Article 21(2), which in turn claims the benefit of the earlier filing date of U.S. Provisional Application No. 62/736,246, filed Sep. 25, 2018, each of which is incorporated by reference in its entirety herein.

FIELD

This disclosure concerns halogenated analogs of 5-aza-2'-deoxycytidine, such as halogenated analogs of 5-aza-4'-thio-2'-deoxycytidine (5-aza-T-dCyd), and methods of using the halogenated analogs.

SUMMARY

Halogenated analogs of 5-aza-2'-deoxycytidine and methods of using the halogenated analogs are disclosed. In some embodiments, the compounds have a structure according to formula Ia, or a stereoisomer, tautomer, or pharmaceutically acceptable salt thereof:

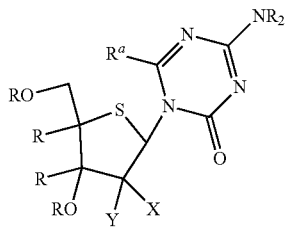

Ia where X is halo; Y is hydrogen, halo, or deuterium; each R independently is hydrogen or deuterium; and $R^a$ is hydrogen, deuterium, alkyl, alkoxy, amino, or halo. In certain embodiments, (i) X is F; or (ii) Y is hydrogen; or (iii) each R is hydrogen; or (iv) $R^a$ is hydrogen; or (v) any combination of (i), (ii), (iii), and (iv).

In some embodiments, the compound has a structure according to any one of formulas IIa-Va, or any combination thereof:

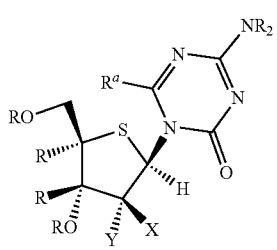

IIa

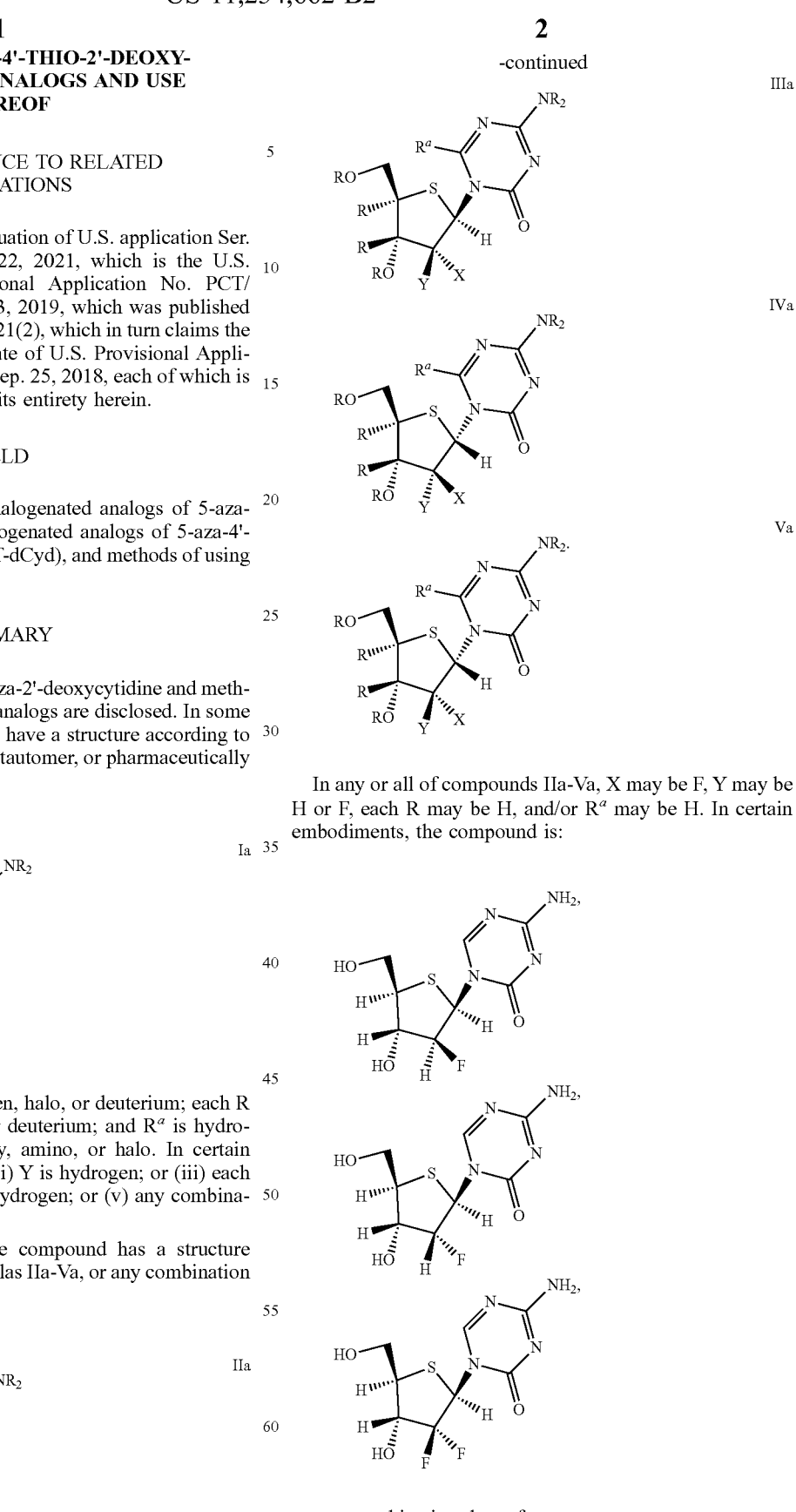

In any or all of compounds IIa-Va, X may be F, Y may be H or F, each R may be H, and/or $R^a$ may be H. In certain embodiments, the compound is:

or any combination thereof.

A pharmaceutical composition may include at least one of the disclosed compounds and a pharmaceutically acceptable carrier. In some embodiments, the pharmaceutical composition is formulated for intravenous, oral, intraperitoneal, subcutaneous, rectal, or buccal administration.

A method of inhibiting a neoplasia includes contacting neoplastic cells with an effective amount of a compound as disclosed herein. In some embodiments, contacting the neoplastic cells with the effective amount of the compound reduces proliferation of the neoplastic cells.

In any or all embodiments, contacting the neoplastic cells with the effective amount of the compound may include administering a therapeutically effective amount of the compound to a subject having or suspected of having a disease characterized at least in part by presence of neoplastic cells, for example, a cancer. In some examples, the cancer is a cancer of the kidney, bladder, breast, colon, endometrium, skin, blood, pancreas, prostate, bone, liver, lung, esophagus, or central nervous system. In any or all embodiments, administering the therapeutically effective amount of the compound to the subject may reduce a sign or symptom of the disease. In one embodiment, the sign or symptom of the disease is a solid tumor and administering the therapeutically effective amount of the compound to the subject reduces growth of the solid tumor, reduces a volume of the solid tumor, reduces metastasis of the solid tumor, or any combination thereof. In another embodiment, the sign or symptom of the disease is an abnormal complete blood count and administering the therapeutically effective amount of the compound to the subject at least partially normalizes the complete blood count. In any or all embodiments, administering the therapeutically effective amount of the compound may include administering a pharmaceutical composition comprising the therapeutically effective amount of the compound to the subject.

The foregoing and other objects, features, and advantages of the invention will become more apparent from the following detailed description, which proceeds with reference to the accompanying figures.

BRIEF DESCRIPTION OF THE DRAWINGS

FIGS. 6A and 6B show GI50 data for Compound 1 and 5-aza-T-dCyd, respectively, against non-small cell lung cancer cell lines.

DETAILED DESCRIPTION

Figure 1:
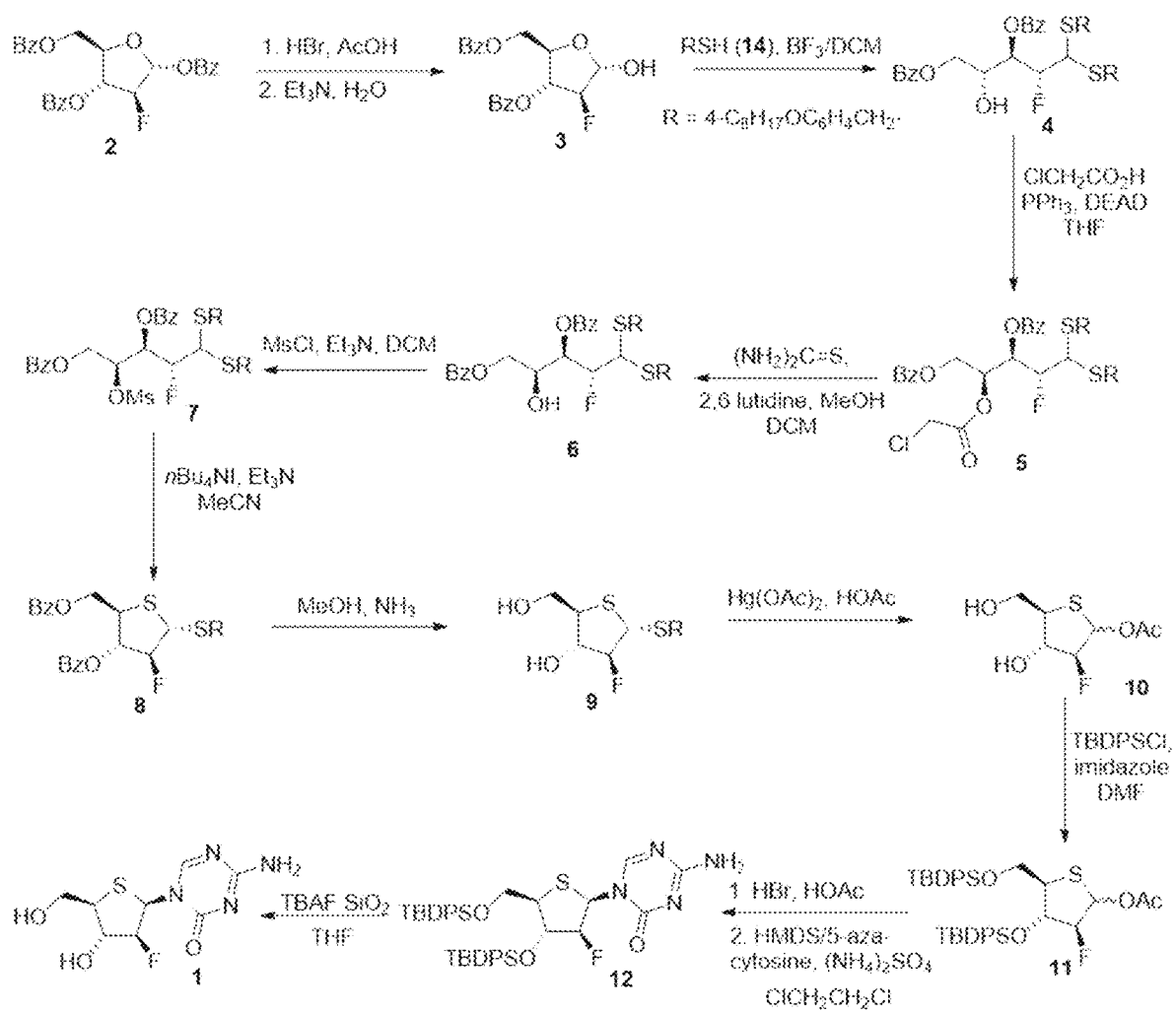
FIG. 1 is an exemplary synthesis scheme for 4-amino-1-((2R,3S,4S,5R)-3-fluoro-4-hydroxy-5-(hydroxymethyl)tetrahydrothiophen-2-yl)-1,3,5-triazin-2(1H)-one (Compound 1).

Halogenated analogs of 5-aza-2'-deoxycytidine and methods of using the halogenated analogs are disclosed. In some embodiments, the compounds are halogenated analogs of 5-aza-4'-thio-2'-deoxycytidine (5-aza-T-dCyd). The disclosed compounds may be useful for treating diseases characterized at least in part by the presence of neoplastic cells, such as cancers. Some embodiments of the disclosed halogenated analogs may be more efficacious with respect to treating certain cancers, than the corresponding non-halogenated aza compounds and/or corresponding halogenated, but non-aza analogs.

I. DEFINITIONS AND ABBREVIATIONS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximates unless the word "about" is recited.

Although there are alternatives for various components, parameters, operating conditions, etc. set forth herein, that does not mean that those alternatives are necessarily equivalent and/or perform equally well. Nor does it mean that the alternatives are listed in a preferred order unless stated otherwise.

Definitions of common terms in chemistry may be found in Richard J. Lewis, Sr. (ed.), *Hawley's Condensed Chemical Dictionary*, published by John Wiley & Sons, Inc., 1997 (ISBN 0-471-29205-2). In order to facilitate review of the various embodiments of the disclosure, the following explanations of specific terms are provided:

Active agent: A drug, medicament, pharmaceutical, therapeutic agent, nutraceutical, or other compound administered to a subject to effect a change, such as treatment, amelioration, or prevention of a disease or disorder or at least one symptom associated therewith. The term active agent also includes biological active agents such as proteins, antibodies, antibody fragments, peptides, oligonucleotides, vaccines, and various derivatives of such materials.

Alkyl: A hydrocarbon group having a saturated carbon chain. The chain may be cyclic, branched or unbranched. Examples, without limitation, of alkyl groups include methyl, ethyl, propyl, butyl, pentyl, hexyl, heptyl, octyl, nonyl and decyl.

Alkoxy: A radical (or substituent) having the structure —OR, where R is a substituted or unsubstituted alkyl. Methoxy (—OCH$_3$) is an exemplary alkoxy group. In a substituted alkoxy, R is alkyl substituted with a non-interfering substituent.

Anomer: An epimer (an isomer having a different configuration at just one chiral carbon) occurring in cyclic saccharides.

Co-administration: The terms "co-administration" and "co-administering" refer to administration of a compound disclosed herein with at least one other active agent within the same general time period, and does not require administration at the same exact moment in time (although co-administration is inclusive of administering at the same exact moment in time). Thus, co-administration may be on the same day or on different days, or in the same week or in different weeks.

Effective amount or therapeutically effective amount: An amount sufficient to provide a beneficial, or therapeutic, effect to a subject or a given percentage of subjects.

Inhibit: As used herein, the term "inhibit" means to reduce or prevent.

Neoplasia/neoplasm/neoplastic: A neoplasia is an abnormal growth of tissue or blood cells. The abnormal growth may form a solid mass or tumor. A neoplasm can be benign, in situ (e.g., a non-invasive cancer or precancerous neoplasm) or malignant (e.g., a cancer).

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of one or more cyanine fluorophores as disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutically acceptable salt: A biologically compatible salt of a disclosed cyanine fluorophores, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. Pharmaceutically acceptable acid addition salts are those salts that retain the biological effectiveness of the free bases while formed by acid partners that are not biologically or otherwise undesirable, e.g., inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Pharmaceutically acceptable base addition salts include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19, which is incorporated herein by reference.)

Stereochemistry: The three-dimensional spatial configuration of a molecule.

Stereoisomer: Isomers that have the same molecular formula and sequence of bonded atoms, but which differ only in the three-dimensional orientation of the atoms in space.

Subject: An animal or human subjected to a treatment, observation or experiment.

Tautomers: Constitutional isomers of organic compounds that differ only in the position of the protons and electrons, and are interconvertible by migration of a hydrogen atom. Tautomers ordinarily exist together in equilibrium.

Treat/treatment: As used herein, the terms "treat" and "treatment" mean to inhibit (reduce or prevent) at least one sign or symptom associated with a condition, i.e., a disorder or disease. With respect to a tumor, treating may mean reducing or preventing tumor growth, reducing a tumor volume, and/or reducing or preventing tumor metastasis. Treatment may, for example, produce a reduction in severity of some or all clinical symptoms of the tumor, a slower progression of the tumor (for example by prolonging the life of a subject having the tumor), a reduction in the number of tumor reoccurrence, an improvement in the overall health or well-being of the subject, or by other parameters well known in the art that are specific to the particular disorder or disease.

II. HALOGENATED ANALOGS OF 5-AZA-2'-DEOXYCYTIDINE

Halogenated analogs of 5-aza-2'-deoxycytidine and stereoisomers thereof have a structure according to general formula I:

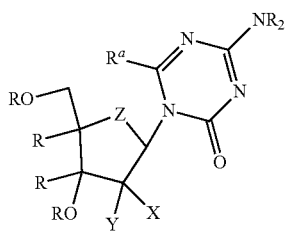

where X is halo (F, Cl, Br, or I), Y is hydrogen, halo (F, Cl, Br, or I), or deuterium, Z is S or O each R independently is hydrogen or deuterium, and $R^a$ is hydrogen, deuterium, alkyl (e.g., $C_{1-5}$ or $C_{1-3}$ alkyl, such as methyl, ethyl, n-propyl, or isopropyl) alkoxy, amino, or halo. In some embodiments, Z is S. In any or all embodiments, X may be F. In any or all embodiments, Y may be hydrogen or F. In any or all embodiments, each R may be hydrogen. In any or all embodiments, $R^a$ may be hydrogen.

In some embodiments, the compound is a halogenated analog of 5-aza-4'-thio-2'-deoxycitidine (5-aza-T-dCyd) and has a structure according to general formula Ia where X, Y, R, and $R^a$ are as defined above:

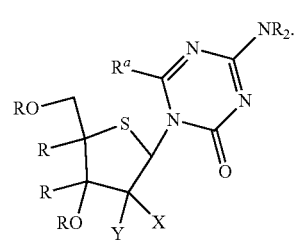

The halogenated analogs may have a stereochemistry according to any one of formulas II-V or any combination thereof, where X, Y, Z, R, and $R^a$ are as defined above:

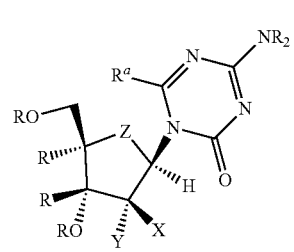

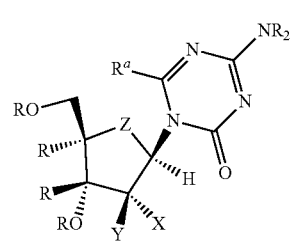

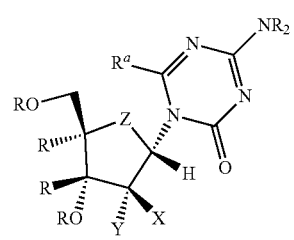

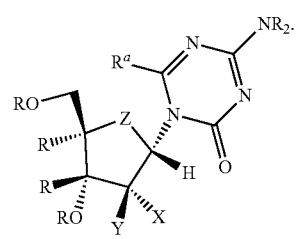

In some embodiments, Z is S, and the compound has a structure according to anyone of formulas IIa-Va, or any combination thereof:

IIa
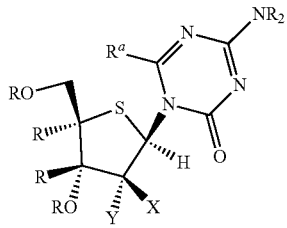
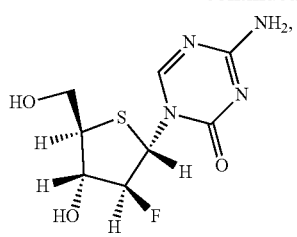
IIIa
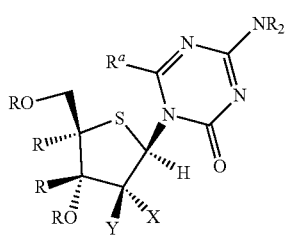
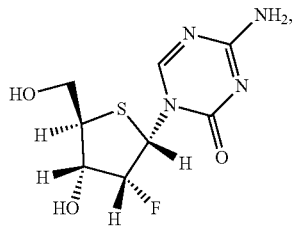
IVa
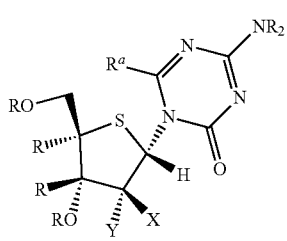
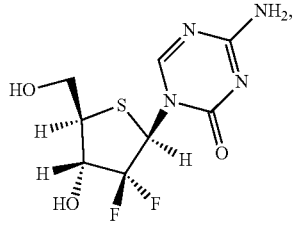
Va
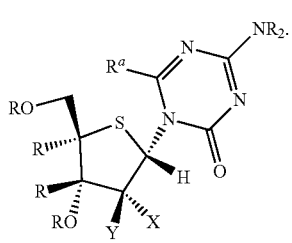
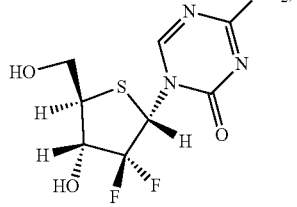
or any combination thereof.
In certain embodiments, the compound is a β-anomer, i.e., a compound according to formula II, IIa, III, or IIIa.
Exemplary compounds include, but are not limited to:
In some embodiments, the compound is
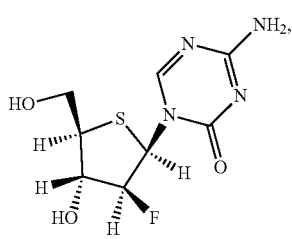
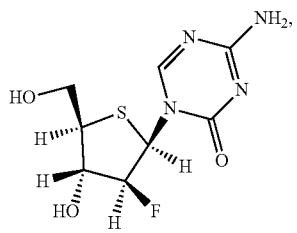
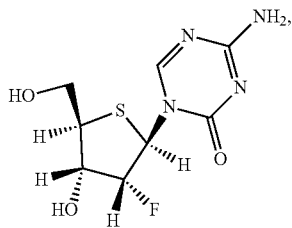
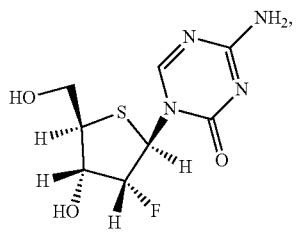

-continued

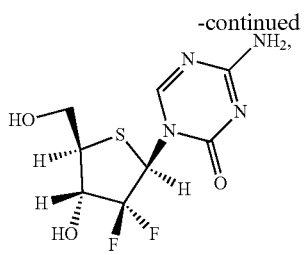

or any combination thereof.

In certain embodiments, the compound is:

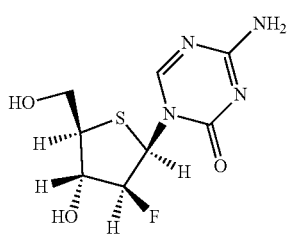 [SMILES: Nc1ncn([C@@H]2S[C@H](CO)[C@@H](O)[C@@H]2F)c(=O)n1]

4-amino-1-((2R,3S,4S,5R)-3-fluoro-4-hydroxy-5-(hydroxymethyl)tetrahydrothiophen-2-yl)-1,3,5-triazin-2(1H)-one

III. PHARMACEUTICAL COMPOSITIONS

This disclosure also includes pharmaceutical compositions comprising at least one compound as disclosed herein. Some embodiments of the pharmaceutical compositions include a pharmaceutically acceptable carrier and at least one compound. The pharmaceutical compositions can also include one or more additional active ingredients such as anti-cancer agents, anti-inflammatory agents, antiviral agents, antimicrobial agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), for example, describes compositions and formulations suitable for pharmaceutical delivery of the compounds herein disclosed.

The compounds according to Formula I disclosed herein can be administered to subjects by a variety of routes, including by parenteral, oral, or rectal routes. Parenteral routes include, but are not limited to, intravenous, intraperitoneal, subcutaneous, buccal, and sublingual routes. In other alternative embodiments, the compounds can be administered ex vivo by direct exposure to cells, tissues or organs originating from a subject. Ex vivo administration may be useful, for example, to determine whether a cell (e.g., a cancer cell) is responsive to administration of the compound.

The pharmaceutical compositions may be in a dosage unit form such as an injectable fluid, an oral delivery fluid (e.g., a solution or suspension), a nasal delivery fluid (e.g., for delivery as an aerosol or vapor), a semisolid form (e.g., a topical cream), or a solid form such as powder, pill, tablet, or capsule forms.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

To formulate the pharmaceutical compositions, the compounds can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, isotonizing agents (for example, sodium chloride, mannitol, sorbitol), adsorption inhibitors (for example, Tween® 80 polyethylene sorbitol ester or Miglyol® 812 triglycerides), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compounds can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compounds can be combined with the base or vehicle according to a variety of methods, and release of the compounds can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain, as pharmaceutically acceptable vehicles, substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compounds can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compounds can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active compound and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-caprolactone-CO-lactic acid), poly(epsilon.-caprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compounds can be delivered to a subject in a manner consistent with conventional methodologies associated with management of the disorder for which treatment or prevention is sought. In accordance with the disclosure herein, a prophylactically or therapeutically effective amount of the compound(s) is administered to a subject in need of such treatment for a time and under conditions sufficient to inhibit and/or treat a disease (e.g., a cancer) or one or more symptom(s) thereof.

The compounds can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosages of the compounds can be provided as repeated doses within a prolonged prophylaxis or treatment regimen that will yield clinically significant results to alleviate one or more symptoms or detectable conditions associated with a targeted condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art.

IV. METHODS OF USE

In some embodiments, a compound according to formula I, or a stereoisomer, tautomer, or pharmaceutically acceptable salt thereof, inhibits a neoplasia when neoplastic cells are contacted with an effective amount of the compound. Inhibition of a neoplasia includes reducing a sign or symptom associated with the neoplasia, such as a rate of growth or proliferation of neoplastic cells relative to a rate of proliferation in the absence of the compound. When the neoplasia is a solid tumor, inhibiting the neoplasia may reduce or prevent tumor growth, reduce tumor volume, and/or reduce metastasis of the solid tumor.

Neoplasias may be benign, in situ/precancerous, or malignant. In some embodiments, the neoplasia is malignant—that is, a cancer—and contacting the cancer cells with an effective amount of the compound according to formula I reduces or prevents proliferation of the cancer cells. Cancers that may be inhibited or treated by administration of the disclosed compounds include, but are not limited to, cancers of the kidney (renal cell), bladder, breast (male and female), colon, endometrium, lung (including bronchus), skin (including melanoma), blood (e.g., leukemia, lymphoma (for example, non-Hodgkin's lymphoma), myeloma), pancreas, prostate, bone, liver, lung, esophagus, and central nervous system cancers.

Contacting neoplastic cells with the compound according to formula I may be performed in vitro, in vivo, or ex vivo. When ascertaining whether the compound might be effective against a particular neoplasia, the cells may be contacted in vitro (for example, in a cell culture) or ex vivo (for example, in a biological sample obtained from a subject) to determine whether the compound reduces or prevents cellular growth and/or proliferation.

In some embodiments, contacting neoplastic cells with the effective amount of the compound comprises administering a therapeutically effective amount of the compound to a subject having or suspected of having a disease characterized at least in part by presence of neoplastic cells. The subject may be a mammal, such as a human or a non-human mammal (for example, a dog, cat, horse, rabbit, or the like). In certain embodiments, the neoplastic cells are malignant and the disease is a cancer. In any or all embodiments, administering the therapeutically effective amount of the compound to the subject may reduce a sign or symptom of the disease. In some embodiments, the sign or symptom is a solid tumor and administering the therapeutically effective amount of the compound to the subject reduces growth of the solid tumor, reduces a volume of the solid tumor, reduces metastasis of the solid tumor, or any combination thereof. In other embodiments, the sign or symptom may be an abnormal complete blood count and administering the therapeutically effective amount of the compound to the subject partially or fully normalizes the complete blood count. Other signs of symptoms of a disease characterized at least in part by presence of neoplastic cells include, but are not limited to, coughing, shortness of breath, coughing up blood, swelling, pain, fever, chills, frequent infections, itchy skin or rash, loss of appetite, nausea, night sweats, persistent weakness, fatigue, shortness of breath, bloating, changes in bowel or bladder habits, constipation, diarrhea, bloody stools, rectal bleeding, jaundice, abnormal vaginal bleeding, difficulty swallowing, voice changes, mouth sores, dry mouth, flu-like symptoms, headaches, easy bruising or bleeding, enlarged lymph nodes, and changes in appearance of a mole.

Administering the therapeutically effective amount of the compound may comprise administering a pharmaceutical composition comprising the therapeutically effective amount of the compound to the subject. Administration may be by any suitable route including, but not limited to, intravenous, oral, intraperitoneal, subcutaneous, rectal, or buccal administration.

The actual dosages of the compounds will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the agent for eliciting the desired activity or biological response in the subject. Dosage regimens can be adjusted to provide an optimum prophylactic or therapeutic response. A therapeutically effective amount is also one in which any toxic or detrimental side effects of the compound is outweighed in clinical terms by therapeutically beneficial effects.

Alternatively, effective dosages can be determined using in vitro models. Using such models, only ordinary calculations and adjustments are required to determine an appropriate concentration and dose to administer a therapeutically effective amount of the compound (for example, amounts that are effective to elicit a desired immune response or alleviate one or more symptoms of a targeted disease). In alternative embodiments, an effective amount or effective dose of the compounds may simply inhibit or enhance one or more selected biological activities correlated with a disease or condition, as set forth herein, for either therapeutic or diagnostic purposes.

A non-limiting range for a therapeutically effective amount of a compound according to formula I within the methods and formulations of the disclosure is from 0.0001 grams to 100 grams for an adult human, such as from 0.001 grams to 50 grams, 0.01 grams to 25 grams, or 0.1 grams to 10 grams. In some embodiments, the therapeutically effective amount is within a range of from 0.001 mg/kg body weight to 100 mg/kg body weight, such as 0.01 mg/kg body weight to 20 mg/kg body weight, 0.01 mg/kg body weight to 10 mg/kg body weight 0.05 mg/kg to 5 mg/kg body weight, or 0.1 mg/kg to 2 mg/kg body weight. The therapeutically effective amount may be administered in a single dose or split into two or more doses administered over time. In some embodiments, the therapeutically effective amount of the compound, or a pharmaceutical composition comprising the compound, is administered to a subject in a dosing regimen of once, twice, or three times daily. The dosing regimen may include dosing holidays of 1-14 days.

Dosage can be varied by the attending clinician to maintain a desired concentration at a target site (for example, systemic circulation). Higher or lower concentrations can be selected based on the mode of delivery, for example, oral delivery versus intravenous or subcutaneous delivery. Dosage can also be adjusted based on the release rate of the administered formulation, for example, of sustained release oral versus injected particulate or rectal suppository, and so forth.

In some embodiments, a second active agent may be co-administered with the compound. The compound and the second active agent may be administered either separately or together in a single composition. The second active agent may be administered by the same route or a different route. The compound and the second agent may be administered concurrently or at separate times. Separate administration may be performed in any sequence. If administered concurrently, the compound and the second active agent may be combined in a single pharmaceutical composition or may be administered concurrently as two pharmaceutical compositions. The second active agent may be, for example, an anti-cancer agent, an anti-inflammatory agent, an antimicrobial agent, an antiviral agent, an anesthetic agent, or the like.

Illustrative anti-cancer agents include, but are not limited to, abiraterone, actinomycin D, altretamine, amifostine, anastrozole, asparaginase, bexarotene, bicalutamide, bleomycin, buserelin, busulfan, carboplatin, carmustine, chlorambucil cisplatin, cladribine, clodronate, combretastatin A4, cyclophosphamide, cyproterone, cytarabine, dacarbazine, daunorubicin, degarelix, diethylstilbestrol, docetaxel, doxorubicin, duocarmycin DM, epirubicin, ethinyl estradiol, etoposide, exemestane, 5-fluorouracil, fludarabine, flutamide, folinic acid, fulvestrant, gemcitabine, goserelin, ibandronic acid, idarubicin, ifosfamide, irinotecan, lanreotide, lenalidomide, letrozole, leuprorelin, medroxyprogesterone, megestrol, melphalan, mesna, methotrexate, octreotide, pamidronate, pemetrexed, mitocmycin, mitotane, mitoxantrone, oxaliplatin, paclitaxel, pentastatin, pipbroman, plicamycin, procarbazine, raltitrexed, stilbestrol, streptozocin, tamoxifen, temozolomide, teniposide, topotecan, triptorelin, vinblastine, vincristine, vinorelbine, and zolendronic acid.

V. EXAMPLES

Example 1

Figure 2:
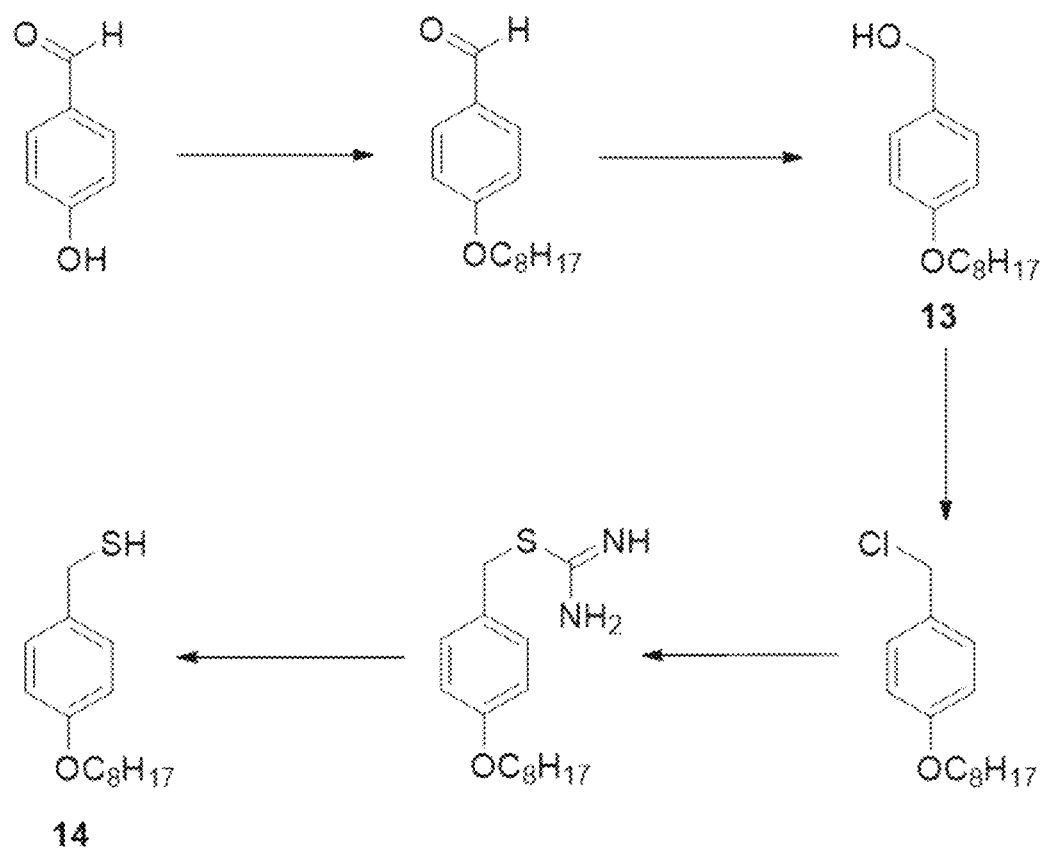
FIG. 2 is an exemplary synthesis scheme for 4-oxyloxyphenylmethanethiol.

Synthesis of 4-amino-1-((2R,3S,4S,5R)-3-fluoro-4-hydroxy-5-(hydroxymethyl)tetrahydrothiophen-2-yl)-1,3,5-triazin-2(1H)-one FIG. 1 is an exemplary synthesis scheme for 4-amino-1-((2R,3S,4S,5R)-3-fluoro-4-hydroxy-5-(hydroxymethyl)tetrahydrothiophen-2-yl)-1,3,5-triazin-2(1H)-one (Scheme 1). FIG. 2 is an exemplary synthesis scheme for precursor 4-oxyloxyphenylmethanethiol (Scheme 2).

4-Octyloxyphenylmethanol (13)

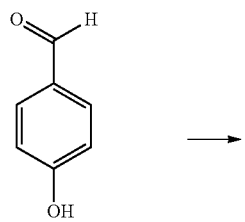

Chemical Formula : C$_7$H$_6$O$_2$
Molecular Weight: 122.12

-continued

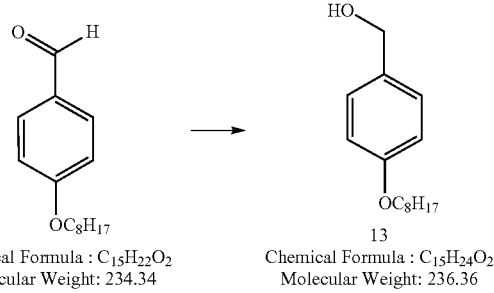

Chemical Formula : C$_{15}$H$_{22}$O$_2$
Molecular Weight: 234.34

Chemical Formula : C$_{15}$H$_{24}$O$_2$
Molecular Weight: 236.36

Preparation: A mixture of 4-hydroxybenzaldehyde (998.0 g, 8.17 mol), 1-bromooctane (1664.2 g, 8.617 mol) and potassium carbonate (1164.2 g, 8.436 mol) in acetonitrile (8.0 L) was refluxed overnight and cooled to ambient temperature. The solid was filtered off, and the filtrate was concentrated under reduced pressure to give 1959.0 g (102.3%) of crude 4-octyloxybenzaldehyde. Product was dissolved in methanol (6.0 L) and sodium borohydride (100.0 g, 2.64 mol) was added portion-wise to the formed solution while keeping the temperature below 15° C. The reaction mixture was stirred at ambient temperature for 1 h. A solution of sodium hydroxide (33.3 g, 832.5 mmol) in water (500 mL) was added, followed by ethyl acetate (3.0 L) and brine (3.0 L). The organic solution was separated, dried over sodium sulfate and evaporated under reduced pressure. Heptane (2 L) was added to the residue and the formed mixture was cooled to 4° C. The resulting solid was filtered off, washed with ice-cooled heptane and dried in vacuum to give 1715.0 g (88.8%) of crude 4-octyloxyphenylmethanol (13), which was used in the following step without further purification.

$^1$H NMR (300 MHz, CDCl$_3$/TMS) d 7.26 (d, J=8.7 Hz, 2H); 6.87 (d, J=8.7 Hz, 2H); 4.59 (s, 2H); 3.95 (t, J=6.6 Hz, 2H); 1.73-1.81 (m, 3H); 1.30-1.48 (m, 10H); 0.89 (t, J=6.9 Hz, 3H) ppm.

4-Octyloxyphenylmethanethiol (14)

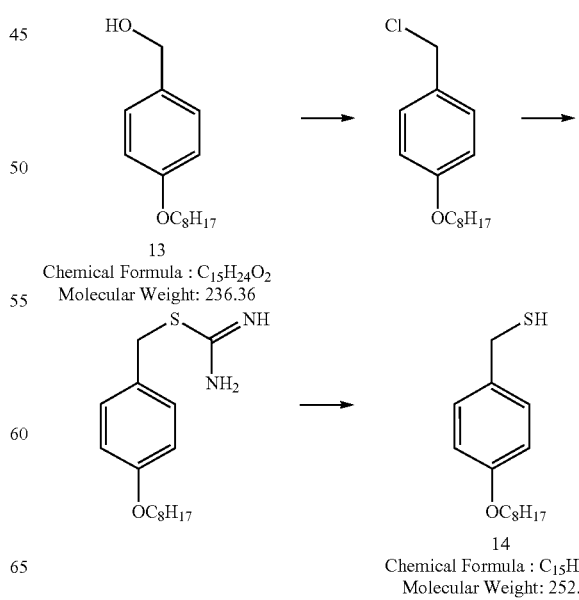

13
Chemical Formula : C$_{15}$H$_{24}$O$_2$
Molecular Weight: 236.36

14
Chemical Formula : C$_{15}$H$_{24}$OS
Molecular Weight: 252.42

Preparation: A mixture of 4-octyloxyphenylmethanol (13) (1716.2 g, 7.26 mol), concentrated HCl (1345 mL, 16.41 mol) and acetonitrile (3.8 L) was stirred overnight at ambient temperature. Then, thiourea (663.8 g, 8.72 mol) and acetonitrile (1.3 L) were added. The mixture was heated to reflux for 2 h, cooled to room temperature and kept overnight. A solution of sodium hydroxide (12162.7 g, 29.07 mol) in water (2.3 L) was added. The mixture was heated to reflux for 3 h and cooled to 10° C. Concentrated HCl (1.34 L) was added while keeping the temperature below 15° C. The mixture was extracted with methyl t-butyl ether (7 L). The extract was dried over magnesium sulfate and concentrated under reduced pressure. Heptane (2.2 L) was added to the residue, and the mixture was evaporated. Heptane (3.4 L) was again added to the residue. The formed milky solution was kept overnight and filtered through a silica gel pad (1.0 kg). The filtrate was evaporated to give 1636.0 g (89.3%) of 4-octyloxyphenylmethanethiol (14).

$^1$H NMR (300 MHz, CDCl$_3$/TMS) d 7.23 (d, J=8 Hz, 2H); 6.83 (d, J=8 Hz, 2H); 3.95 (m, 2H); 3.72 (d, J=7.5 Hz, 2H); 1.75 (m, 3H); 1.25 (m, 9H); 0.87 (m, 3H) ppm.

(2R,3R,4S,5S)-3-(Benzoyloxy)-4-fluoro-5-hydroxytetrahydrofuran-2-yl)methyl benzoate (3)

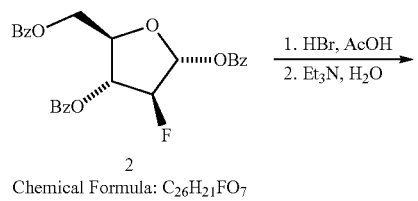

2
Chemical Formula: C$_{26}$H$_{21}$FO$_7$
Molecular Weight: 464.45

3
Chemical Formula: C$_{19}$H$_{17}$FO$_6$
Molecular Weight: 360.34

Preparation: To a solution of (2R,3S,4R,5R)-5-((benzoyloxy)methyl)-3-fluorotetrahydrofuran-2,4-diyl dibenzoate (2) (176 g, 379 mmol) in dichloromethane (600 mL) in a 3000 mL one neck round bottom flask under nitrogen was added hydrobromic acid, 33% in acetic acid (131 mL, 796 mmol) and the reaction was stirred 6 hours at rt. The solution was poured into a vigorously stirred mixture of 1200 mL saturated sodium bicarbonate, solid sodium bicarbonate (121 g, 1440 mmole) and 1200 mL dichloromethane held at 0° C. The layers were separated and the organic layer was washed with 1×100 mL saturated sodium bicarbonate, dried over anhydrous magnesium sulfate, and concentrated in vacuo to provide 136 g (84%) of the intermediate bromide as a pale yellow oil. $^1$H NMR (400 MHz, Chloroform-d) δ 8.14-7.99 (m, 3H), 7.66-7.45 (m, 2H), 7.50-7.43 (m, 1H), 7.48-7.37 (m, 1H), 6.62 (m, 1H), 5.59-5.47 (m, 1H), 4.87-4.64 (m, 2H) ppm.

The crude bromide was dissolved in DMF (600 mL) in a 3000 mL one-neck round-bottom flask under ambient atmosphere. The solution was treated with triethylamine (317 mL, 2274 mmol) and water (205 mL, 1.14E+04 mmol) and the reaction was stirred at room temperature. The reaction showed an exotherm from 23 to 37° C. upon addition of water/triethylamine mixture. The reaction was stirred for 1 h and then it was diluted with 2400 mL ethyl acetate. After stirring vigorously with 1200 mL 50% saturated sodium chloride, the layers were separated, and the organic layer was washed with 3×500 mL 50% saturated sodium chloride. The organic layer was filtered through anhydrous magnesium sulfate and the filtrate was concentrated in vacuo to afford 116 grams (85%) of the title compound (3) as a viscous amber oil. It was elected to use the crude oil directly, without further purification.

$^1$H NMR (400 MHz, Chloroform-d) δ 8.07-8.02 (m, 1H), 8.06-7.99 (m, 2H), 8.04-7.91 (m, 1H), 7.63-7.28 (m, 6H), 5.66 (dd, J=10.4, 0.9 Hz, 1H), 5.46 (ddd, J=22.3, 4.5, 1.0 Hz, 1H), 5.21-5.06 (m, 1H), 4.78-4.54 (m, 4H) ppm.

(2R,3R,4S)-4-Fluoro-2-hydroxy-5,5-bis((4-(octyloxy)benzyl)thio)pentane-1,3-diyl dibenzoate (4)

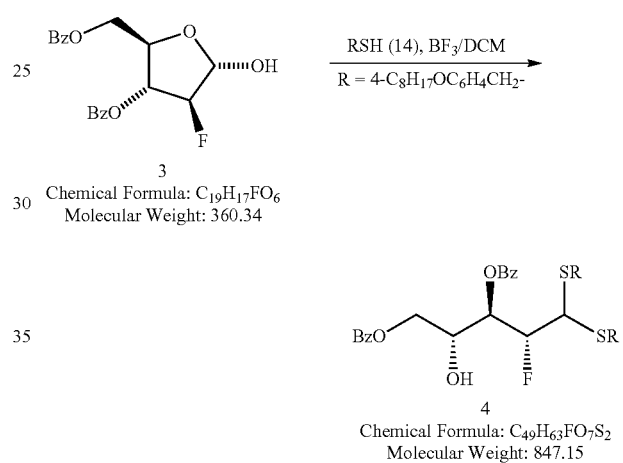

3
Chemical Formula: C$_{19}$H$_{17}$FO$_6$
Molecular Weight: 360.34

4
Chemical Formula: C$_{49}$H$_{63}$FO$_7$S$_2$
Molecular Weight: 847.15

Preparation: A 2,000 mL one-neck round-bottom flask under nitrogen was charged with ((2R,3R,4S,5S)-3-(benzoyloxy)-4-fluoro-5-hydroxytetrahydrofuran-2-yl)methyl benzoate (3) (58 g, 161 mmol) and (4-(octyloxy)phenyl)methanethiol (102 g, 402 mmol) (14) in 500 mL dichloromethane. The solution was cooled to 0° C. and was treated dropwise with boron trifluoride diethyletherate (39.7 mL, 322 mmol) in 50 mL dichloromethane. The reaction was stirred for 1.5 h at 0° C. and was added rapidly drop-wise to an ice-cooled solution of potassium carbonate (150 g, 1.08 moles) in 600 mL water layered with 200 mL dichloromethane. The mixture was filtered through celite 503, and the layers were separated. The organic layer was dried over anhydrous magnesium sulfate, and the filtrate was concentrated in vacuo to an amber oil. The oil was diluted with hexane, loaded onto a 125 G RediSep® Rf column (Teledyne ISCO) and was eluted over a 340 G UltraSil SNAP cartridge (Biotage, Charlotte, N.C.) with a 0-20% ethyl acetate/hexane gradient into 27 mL fractions on a Biotage® system. Fractions 28-100 were combined and concentrated to afford 85 g (62%) of the title compound (4) as a golden oil.

$^1$H NMR (400 MHz, Chloroform-d): δ 8.03-7.93 (m, 2H), 7.94-7.86 (m, 2H), 7.61-7.49 (m, 2H), 7.40 (m, 4H), 7.19-7.10 (m, 2H), 6.97-6.88 (m, 2H), 6.71-6.62 (m, 2H), 6.57-6.48 (m, 2H), 5.65 (ddd, J=26.9, 7.7, 1.7 Hz, 1H), 5.01 (ddd, J=45.2, 9.1, 1.8 Hz, 1H), 4.45 (dd, J=11.7, 2.9 Hz, 1H), 4.34-4.17 (m, 2H), 3.97-3.62 (m, 8H), 2.73 (d, J=6.2 Hz, 1H), 1.80-1.65 (m, 4H), 1.49-1.32 (m, 4H), 1.37-1.20 (m, 17H), 0.92-0.81 (m, 6H).

(2S,3R,4S)-2-(2-chloroacetoxy)-4-fluoro-5,5-bis((4-(octyloxy)benzyl)thio)pentane-1,3-diyl Dibenzoate (5)

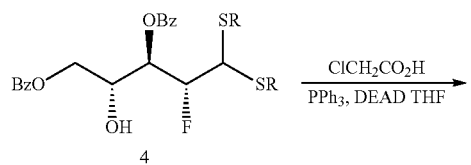

4
Chemical Formula: $C_{49}H_{63}FO_7S_2$
Molecular Weight: 847.15

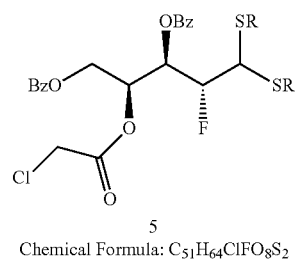

5
Chemical Formula: $C_{51}H_{64}ClFO_8S_2$
Molecular Weight: 923.63

Preparation: An oven-dried 1,000 mL three-neck round-bottom flask under nitrogen was charged with triphenylphosphine (38.7 g, 148 mmol) and 340 mL anhydrous THF. The solution was cooled to −15° C. and was treated dropwise with 40 wt % diethyl azodicarboxylate in toluene (67.2 mL, 148 mmol). The mixture was stirred 1 h as it became heavy with precipitate. The slurry was treated rapidly drop-wise with (2R,3R,4S)-4-fluoro-2-hydroxy-5,5-bis((4-(octyloxy)benzyl)thio)pentane-1,3-diyl dibenzoate (4) (25 g, 29.5 mmol) in 60 mL anhydrous THF. The resulting suspension was treated dropwise with chloroacetic acid (13.94 g, 148 mmol) in 100 mL anhydrous THF. The reaction became briefly homogeneous and then slurried as a white solid precipitated out. The reaction was stirred overnight as the cooling bath expired. The volatiles were removed in vacuo to give a pale yellow paste. The paste was slurried with 900 mL 2:1 hexane/biome (methyl tert-butyl ether) and the insoluble material was removed by filtration. The filtrate was concentrated in vacuo to give 48 g a crude yellow oil. The crude material was dissolved in hexane with a small amount of dichloromethane, was loaded onto a 100 G UltraSil SNAP cartridge and was eluted over a 120 g Zip® Sphere cartridge (Biotage, Charlotte, N.C.) with a 0-20% ethyl acetate/hexane gradient on a Biotage® system. Fractions 4-21 were combined and concentrated to afford 21.70 g (80%) of the title compound (5) as a yellow oil.

¹H NMR (400 MHz, Chloroform-d) δ 8.02-7.86 (m, 4H), 7.63-7.49 (m, 2H), 7.48-7.33 (m, 4H), 7.19-7.11 (m, 2H), 6.97-6.86 (m, 2H), 6.70-6.60 (m, 2H), 6.63-6.52 (m, 2H), 5.92 (ddd, J=25.5, 6.2, 2.4 Hz, 1H), 5.54 (td, J=6.3, 3.2 Hz, 1H), 4.78 (ddd, J=46.0, 8.5, 2.5 Hz, 1H), 4.61-4.44 (m, 2H), 4.37 (ddd, J=12.5, 6.3, 1.2 Hz, 1H), 4.02-3.64 (m, 10H), 1.81-1.66 (m, 4H), 1.49-1.36 (m, 4H), 1.41-1.20 (m, 16H), 0.99-0.80 (m, 6H).

(2S,3R,4S)-4-Fluoro-2-hydroxy-5,5-bis((4-(octyloxy)benzyl)thio)pentane-1,3-diyl dibenzoate (6)

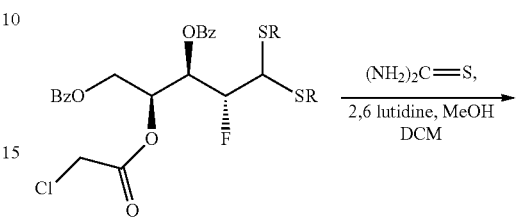

5
Chemical Formula: $C_{51}H_{64}ClFO_8S_2$
Molecular Weight: 923.63

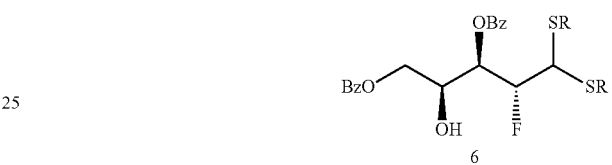

6
Chemical Formula: $C_{49}H_{63}FO_7S_2$
Molecular Weight: 847.15

Preparation: A 1000 mL one-neck round-bottom flask under nitrogen at ambient G-3,3 temperature was charged with (2S,3R,4S)-2-(2-chloroacetoxy)-4-fluoro-5,5-bis((4-(octyloxy)benzyl)thio)pentane-1,3-diyl dibenzoate (5) (21.70 g, 23.49 mmol), dichloromethane (205 mL) and methanol (240 mL). The yellow solution was treated with thiourea (17.88 g, 235 mmol) which caused rapid decolorization of the yellow mixture as the suspension thinned and then became heavier. The suspension was treated dropwise with 2,6-lutidine (2.74 mL, 23.49 mmol) in 35 mL dichloromethane. The heavy suspension gradually achieved near homogeneity within 15 minutes of the lutidine addition. Stirring was continued overnight at room temperature for a total of 23 hours. The reaction was neutralized with citric acid (4.51 g, 23.49 mmol) in water (52 mL), the mixture was diluted with 1 L dichloromethane, and the layers were separated. The organic layer was washed with 1×250 mL 1:1 15% aqueous citric acid and saturated sodium chloride. The layers were separated and the organic layer was dried over anhydrous magnesium sulfate, and concentrated in vacuo to give 21 g of a pale paste. The organic component of the residue was dissolved in 1:3 dichloromethane/hexane, was loaded onto a 100 G UltraSil SNAP cartridge, and was eluted over a 120 G Zip® Sphere cartridge with a 0-20% ethyl acetate/hexane gradient into 27 mL fractions on a Biotage® system. Fractions 24-54 were combined and concentrated to afford 16.98 g (85%) of the title compound (6) as a pale oil.

1H NMR (400 MHz, Chloroform-d) δ 8.03-7.92 (m, 4H), 7.60-7.49 (m, 2H), 7.45-7.34 (m, 4H), 7.12-6.98 (m, 4H), 6.74-6.59 (m, 4H), 5.72 (m, 1H), 5.02 (ddd, J=46.6, 6.3, 4.4 Hz, 1H), 4.40-4.28 (m, 2H), 3.94 (m, 1H), 3.89-3.67 (m, 8H), 2.64 (d, J=6.4 Hz, 1H), 1.71 (m, 4H), 1.49-1.38 (m, 4H), 1.41-1.20 (m, 18H), 0.99-0.80 (m, 6H).

(2S,3R,4S)-4-Fluoro-2-((methylsulfonyl)oxy)-5,5-bis((4-(octyloxy)benzyl)thio)pentane-1,3-diyl dibenzoate (7)

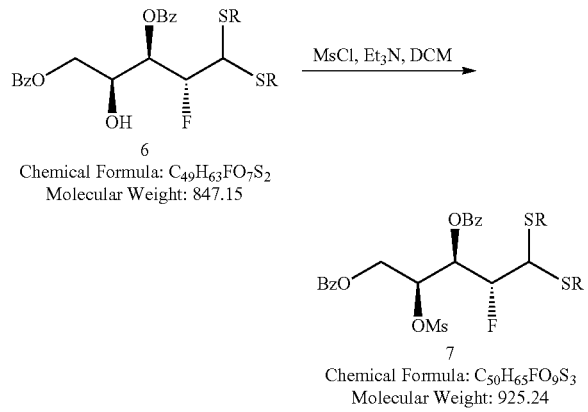

6
Chemical Formula: $C_{49}H_{63}FO_7S_2$
Molecular Weight: 847.15

7
Chemical Formula: $C_{50}H_{65}FO_9S_3$
Molecular Weight: 925.24

Preparation: A 1000 mL one-neck round bottom flask under nitrogen was charged with (2S,3R,4S)-4-fluoro-2-hydroxy-5,5-bis((4-(octyloxy)benzyl)thio)pentane-1,3-diyl dibenzoate (6) (16.95 g, 20.01 mmol) and dichloromethane (200 mL). The solution was cooled to 0° C., treated dropwise with methanesulfonyl chloride (2.03 mL, 26.0 mmol) in 20 mL dichloromethane, followed by drop-wise addition of triethylamine (3.63 mL, 26.0 mmol) in 20 mL dichloromethane. The reaction was stirred for 72 h as the cooling bath expired. The mixture was washed successively with 1×100 mL water, 1×100 mL saturated sodium bicarbonate, and 1×100 mL 1:1 saturated sodium chloride/15% aqueous citric acid. The organic layer was dried over anhydrous magnesium sulfate and concentrated in vacuo to give 17.99 g (97%) of the title compound as a viscous amber oil. Material was used without further purification.

$^1$H NMR (400 MHz, Chloroform-d) δ 7.99 (m, 4H), 7.70-7.49 (m, 2H), 7.49-7.35 (m, 4H), 7.21-7.10 (m, 2H), 7.01-6.85 (m, 2H), 6.77-6.64 (m, 2H), 6.62-6.50 (m, 2H), 5.92 (m, 1H), 5.22-5.14 (m, 1H), 4.85 (m, 1H), 4.68-4.56 (m, 1H), 4.44 (m, 1H), 3.93-3.62 (m, 10H), 2.93 (s, 3H), 1.72 (h, J=6.8 Hz, 4H), 1.50-1.18 (m, 19H), 0.98-0.84 (m, 6H). $^{19}$F NMR (376 MHz, Chloroform-d) δ -188.51 (ddd, J=45.7, 25.7, 11.3 Hz).

((2R,3S,4S)-3-(benzoyloxy)-4-fluoro-5-((4-(octyloxy)benzyl)thio)tetrahydrothiophen-2-yl)methyl benzoate (8)

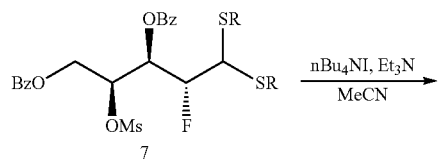

7
Chemical Formula: $C_{50}H_{65}FO_9S_3$
Molecular Weight: 925.24

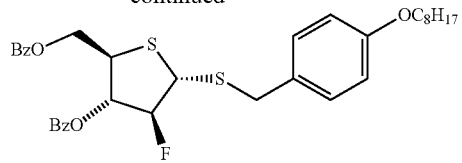

8
Chemical Formula: $C_{34}H_{39}FO_5S_2$
Molecular Weight: 610.80

Preparation: A 3000 mL three-neck round-bottom flask under nitrogen was charged with (2S,3R,4S)-4-fluoro-2-((methylsulfonyl)oxy)-5,5-bis((4-(octyloxy)benzyl)thio)pentane-1,3-diyl dibenzoate (7) (59 g, 63.8 mmol), anhydrous acetonitrile (1000 mL), triethylamine (17.78 mL, 128 mmol), and tetrabutylammonium iodide (47.1 g, 128 mmol). The reaction mixture was heated to reflux for 96 h. The reaction was allowed to cool to rt and the mixture was then poured into 400 mL silica gel (230-400 mesh) and concentrated to dryness. The plug was chromatographed over a 340 G UltraSil SNAP cartridge, eluting with a 0-15% ethyl acetate/hexane gradient on a Biotage® system. Fractions 28-69 were combined and concentrated to give 27.6 g (71%) of the title compound (8) as a viscous oil that crystallized under vacuum to give a cream colored solid. $^{19}$F-NMR indicated a 15:1 C-1 α/β mixture.

$^1$H NMR (400 MHz, Chloroform-d) δ 8.02-7.90 (m, 3H), 7.65-7.47 (m, 2H), 7.47-7.33 (m, 4H), 7.29-7.19 (m, 3H), 6.86-6.76 (m, 2H), 5.97 (ddd, J=9.9, 5.0, 3.9 Hz, 1H), 5.15 (dt, J=50.5, 4.7 Hz, 1H), 4.69-4.42 (m, 3H), 3.97-3.82 (m, 4H), 3.80-3.69 (m, 1H), 1.75 (m, 2H), 1.50-1.19 (m, 10H), 0.95-0.82 (m, 3H). $^{19}$F NMR (376 MHz, Chloroform-d) -187.14 (ddd, J=50.5, 16.6, 9.9 Hz).

(2R,3S,4S)-4-Fluoro-2-(hydroxymethyl)-5-((4-(octyloxy)benzyl)thio)tetrahydrothiophen-3-ol (9)

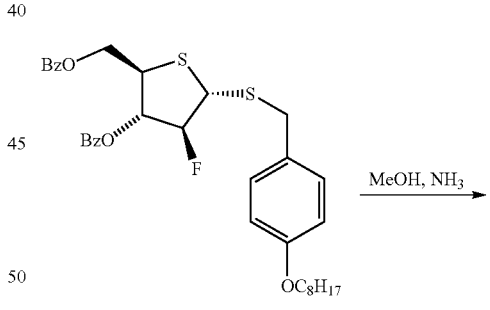

8
Chemical Formula: $C_{34}H_{39}FO_5S_2$
Molecular Weight: 610.80

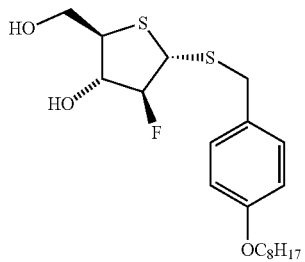

9
Chemical Formula: $C_{20}H_{31}FO_3S_2$
Molecular Weight: 402.58

Preparation: 7M Ammonia in methanol (MeOH) (187 mL, 1310 mmol) was added to a solution of ((2R,3S,4S)-3-(benzoyloxy)-4-fluoro-5-((4-(octyloxy)benzyl)thio)tetrahydrothiophen-2-yl)methyl benzoate (8) (10 g, 16.37 mmol) in dichloromethane (50 mL, 16.37 mmol) and the resulting mixture was stirred at rt. After stirring for 65 h at room temperature the volatiles were removed in vacuo to afford a pasty solid. The solid was stirred with hexane (60 mL) for 1 h at room temperature. The fine white solid was collected, washed with hexane, and dried on the filter to afford 6.60 g (100%) of the title compound (9) as a white solid.

$^1$H NMR (400 MHz, DMSO-$d_6$) δ 7.24-7.16 (m, 2H), 6.90-6.81 (m, 2H), 5.68 (d, J=5.1 Hz, 1H), 5.00 (t, J=5.5 Hz, 1H), 4.85 (dt, J=51.4, 4.9 Hz, 1H), 4.49 (dd, J=16.1, 4.5 Hz, 1H), 4.20 (m, 1H), 3.92 (t, J=6.5 Hz, 2H), 3.91-3.75 (m, 2H), 3.68 (m, 1H), 3.40-3.28 (m, 1H), 3.09 (dddd, J=7.6, 6.1, 4.7, 0.9 Hz, 1H), 1.68 (m, 2H), 1.46-1.33 (m, 2H), 1.28 (m, 8H), 0.90-0.82 (m, 3H).

$^{13}$C NMR (101 MHz, DMSO-$d_6$) δ 158.15, 131.59, 130.42, 129.75, 128.59, 127.86, 114.79, 99.37, 97.49, 75.29, 75.06, 67.81, 64.27, 64.25, 53.22, 53.19, 50.32, 50.13, 36.00, 35.97, 31.67, 29.18, 29.13, 29.10, 25.97, 22.51, 14.38.

$^{19}$F-NMR (400 MHz, DMSO-d6) δ −186.62 (dddd, 1F)

(3S,4S,5R)-3-Fluoro-4-hydroxy-5-(hydroxymethyl)tetrahydrothiophen-2-yl acetate (10)

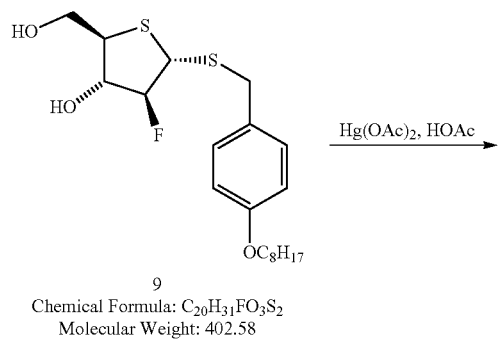

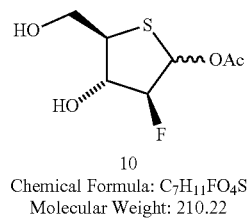

Preparation: A 500 mL one-neck round bottom flask under nitrogen was charged with (2R,3S,4S)-4-fluoro-2-(hydroxymethyl)-5-((4-(octyloxy)benzyl)thio)tetrahydrothiophen-3-ol (37.5 g, 93 mmol) and acetic acid (225 mL, 3972 mmol). The colorless liquid suspension was treated with diacetoxymercury (44.5 g, 140 mmol) in a single portion and the reaction mixture was stirred for 24 h at room temperature. The mixture was diluted with 800 mL heptane and the insoluble material was removed by filtration. The filter cake was washed with 300 mL dichloromethane (DCM) followed by 600 mL heptane and the filtrate was concentrated in vacuo to a pale amber oil. The crude material was taken up in a minimum amount of DCM, was loaded onto a 50 G UltraSIL® SNAP® cartridge (Biotage®, Uppsala, Sweden) and was eluted over a 100 G UltraSIL® SNAP® cartridge and with a 0-50% ethyl acetate/DCM gradient. Fractions 27-92 were combined and concentrated to afford 17.59 g (90%) of the title compound (10) as a 1:1 mixture of anomers.

$^1$H NMR (400 MHz, Chloroform-d) δ 6.02-5.88 (m, 1H), 5.09 (dd, J=7.1, 4.5 Hz, 0.2H), 5.00-4.92 (m, 0.5H), 4.83 (dd, J=9.3, 4.7 Hz, 0.3H), 4.50 (ddd, J=12.1, 9.3, 8.0 Hz, 0.5H), 4.33 (dt, J=14.7, 7.5 Hz, 0.5H), 3.87-3.68 (m, 2H), 3.54 (dtd, J=7.9, 5.1, 1.3 Hz, 0.5H), 3.24 (ddd, J=7.9, 5.3, 4.5 Hz, 0.5H), 2.88 (s, 1H), 2.11 (m, 3H).

$^{19}$F NMR (376 MHz, Chloroform-d) δ −188.81 (dt, J=51.3, 15.2 Hz), −193.39 (dd, J=50.9, 12.2 Hz).

(3S,4S,5R)-4-((tert-butyldiphenylsilyl)oxy)-5-(((tert-butyldiphenylsilyl)oxy)methyl)-3-fluorotetrahydrothiophen-2-yl acetate (11)

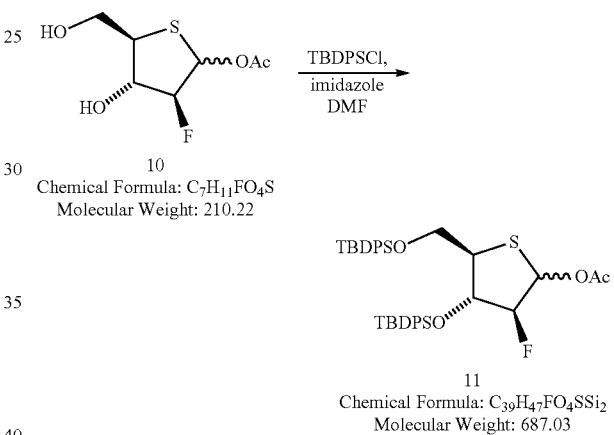

Preparation: (3S,4S,5R)-3-Fluoro-4-hydroxy-5-(hydroxymethyl)tetrahydrothiophen-2-yl acetate (10) (11.85 g, 56.4 mmol) was dissolved in DMF (180 mL) in a 1,000 mL one neck round bottom flask under nitrogen. The solution was treated with imidazole (9.59 g, 141 mmol) followed by tert-butyldiphenylchlorosilane (43.4 mL, 169 mmol) and the reaction mixture was stirred overnight at room temperature. The reaction was diluted with 1,000 mL ethyl acetate and extracted with 1×500 mL 50% saturated sodium chloride followed by 3×150 mL 50% saturated sodium chloride. The organic layer was dried over anhydrous magnesium sulfate and concentrated in vacuo to a colorless oil. The crude material was dissolved in a minimum amount of hexane, was loaded onto a 340 G UltraSil SNAP cartridge, and was eluted with a 0-15% ethyl acetate/hexane gradient into 27 mL fractions on a Biotage® system. Fractions 27-66 were combined and concentrated to afford 36.7 g (95%) of the title compound (11) as a colorless oil.

$^1$H NMR (400 MHz, Chloroform-d) δ 7.78-7.68 (m, 4H), 7.65-7.46 (m, 4H), 7.46-7.20 (m, 12H), 6.07-5.87 (m, 1H), 5.15-4.86 (m, 1H), 4.37-4.19 (m, 1H), 3.81 (qd, J=6.1, 3.1 Hz, 0.4H), 3.64 (m, 1H), 3.41 (m, 1H), 3.25 (ddd, J=24.0, 10.3, 8.5 Hz, 1H), 2.17 (s, 2H), 1.88 (m, 1H), 1.07 (s, 9H), 0.94 (s, 9H). $^{19}$F NMR (376 MHz, Chloroform-d) δ −184.98 (dt, J=49.3, 14.2 Hz), −190.33−−190.64 (m).

4-Amino-1-((2R,3S,4S,5R)-4-((tert-butyldiphenylsilyl)oxy)-5-(((tert-butyldiphenylsilyl)oxy)methyl)-3-fluorotetrahydrothiophen-2-yl)-1,3,5-triazin-2(12)

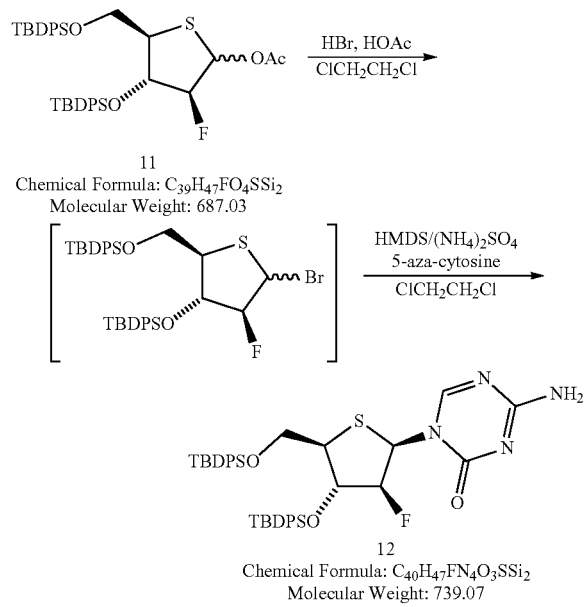

Preparation: HMDS (21.97 mL, 105 mmol) was added to azacytosine (2.91 g, 26.2 mmol) and ammonium sulfate (0.115 g, 0.873 mmol), and the resulting mixture was stirred at 130° C. for 20 h. Excess HMDS was removed under reduced pressure and the remaining residue was suspended in 1,2-dichloroethane (50 mL). Meanwhile, hydrobromic acid (33% in acetic acid) (3.45 mL, 20.96 mmol) was added to a solution of (3S,4S,5R)-4-((tert-butyldiphenylsilyl)oxy)-5-(((tert-butyldiphenylsilyl)oxy)methyl)-3-fluorotetrahydrothiophen-2-yl acetate (11) (6 g, 8.73 mmol) in 1,2-dichloroethane (50 mL) and the resulting mixture was stirred at 0° C. for 2 h. The reaction was quenched with the addition of 75 mL saturated sodium bicarbonate and the mixture was stirred vigorously for 15 min. The layers were separated and the organic layer was dried over anhydrous magnesium sulfate. The solution of intermediate bromide was added to the suspension of silylated azacytosine in a single portion and the white suspension was warmed to 84° C. The suspension became a light slurry as the reaction came to temperature. The reaction was stirred for 5 h at 84° C.

The reaction was cooled to rt overnight, diluted with 75 mL saturated sodium bicarbonate, and stirred for 10 minutes. The slurry was filtered through a bed of Celite® diatomaceous earth and the filter pad was washed with fresh dichloromethane. The layers were separated and the organic layer was dried over anhydrous magnesium sulfate, and concentrated in vacuo to give 5.3 g of an off-white foam. The crude material was dissolved in a minimum amount of dichloromethane, was loaded onto a 50 G UltraSil SNAP cartridge, and was eluted into 27 mL fractions with a 10-65% ethyl acetate/dichloromethane gradient on a Biotage® system. Fractions 19-33 were combined and concentrated to afford 2.7 g (42%) of a white foam. H-NMR indicated the material is a 2:1 f/a mixture.

The white foam was dissolved in 10 mL absolute ethanol (EtOH) and was stirred for 2 h at rt as a fine white solid crystallized from the mixture. The solid was collected, washed with a small amount of EtOH, and dried on the filter to give 630 mg (9%) of pure C-1 alpha anomer as a white solid. The mother liquor was concentrated in vacuo to give 2.07 grams (32%) of the title compound 12 as a white foam (>20:1 C-1 Beta anomer). This material was used without additional fractionation.

Proton, C-1 Alpha Anomer: $^1$H NMR (400 MHz, Chloroform-d) δ 8.85 (s, 1H), 7.53 (ddd, J=14.6, 8.0, 4.2 Hz, 6H), 7.48-7.25 (m, 14H), 6.75 (s, 1H), 6.10 (dd, J=14.0, 1.8 Hz, 1H), 5.72 (s, 1H), 5.09 (dt, J=46.7, 2.0 Hz, 1H), 4.30 (m, 1H), 3.97-3.88 (m, 1H), 3.47 (dd, J=10.2, 6.6 Hz, 1H), 3.43-3.33 (m, 1H), 0.96 (m, 18H).

Fluorine, C-1 Alpha Anomer: $^{19}$F NMR (376 MHz, Chloroform-d) δ −177.38 (dt, J=46.8, 12.5 Hz).

Proton, C-1 Beta Anomer: $^1$H NMR (400 MHz, Chloroform-d) δ 8.41 (d, J=2.6 Hz, 1H), 7.68-7.52 (m, 6H), 7.57-7.42 (m, 4H), 7.47-7.28 (m, 10H), 7.04-6.99 (m, 1H), 6.80 (dd, J=24.5, 3.6 Hz, 1H), 5.69 (s, 1H), 4.81 (dt, J=50.8, 2.8 Hz, 1H), 4.47 (m, 1H), 3.70-3.65 (m, 1H), 3.60-3.44 (m, 2H), 1.10 (s, 9H), 0.89 (s, 9H).

Fluorine, C-1 Beta Anomer: $^{19}$F NMR (376 MHz, Chloroform-d) δ −194.16 (ddd, J=50.5, 24.6, 7.4 Hz).

4-Amino-1-((2R,3S,4S,5R)-3-fluoro-4-hydroxy-5-(hydroxymethyl)tetrahydrothiophen-2-yl)-1,3,5-triazin-2(1H)-one (1)

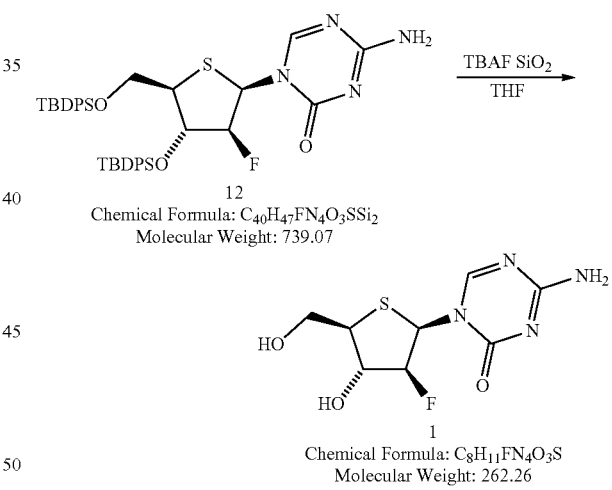

Preparation 1: 4-Amino-1-((2R,3S,4S,5R)-4-((tert-butyldiphenylsilyl)oxy)-5-(((tert-butyldiphenylsilyl)oxy)methyl)-3-fluorotetrahydrothiophen-2-yl)-1,3,5-triazin-2(1H)-one (12) (5.9 g, 7.98 mmol) was dissolved in tetrahydrofuran (45 mL, 555 mmol) in a 200 mL one-neck round-bottom flask under nitrogen. The solution was treated with tetra-n-butylammonium fluoride on silica gel (21.16 g, 29.1 mmol) and was stirred at rt for 1 h. The reaction mixture was treated with 18 g silica gel (230-400 mesh) and concentrated to dryness. The solid plug was chromatographed over a 50 gram UltraSil® SNAP® cartridge while eluting with a 0-12.5% (10% MeOH in IPA)/dichloromethane gradient (0-50% of a 25% (10% MeOH in IPA)/dichloromethane polar phase) into 27 mL fractions on a Biotage® system. Fractions 33-84 were combined and concentrated to afford 1.83 g of a pasty solid. The solid was triturated with 20 mL acetonitrile, was collected by filtration and was dried on the filter to afford 1.48 g (71%) of the title compound (1) an off-white solid.

$^1$H NMR (400 MHz, DMSO-d6) δ 8.78 (d, J=1.3 Hz, 1H), 7.68-7.60 (m, 2H), 6.29 (dd, J=11.6, 5.4 Hz, 1H), 5.92 (d, J=5.2 Hz, 1H), 5.34 (t, J=5.2 Hz, 1H), 5.00 (dt, J=50.7, 5.8 Hz, 1H), 4.27 (m, 1H), 3.68 (m, 2H), 3.23 (q, J=5.5 Hz, 1H) ppm. $^{13}$C NMR (101 MHz, dmso) δ 165.87, 158.07, 158.04, 153.63, 96.79, 94.87, 73.44, 73.21, 61.28, 61.26, 57.44, 57.27, 51.97, 51.93. $^{19}$F NMR (376 MHz, DMSO-d6) δ −192.78 (dt, J=50.6, 11.7 Hz). Melting Point: 208-209° C., d. Combustion Analysis: Calculated: C, 36.64; H, 4.23; F, 7.24; N, 21.36; S, 12.22, Found: C, 36.66; H, 4.14; F, 7.04; N, 21.08; S, 12.27.

Preparation 2: 4-Amino-1-((2R,3S,4S,5R)-4-((tert-butyldiphenylsilyl)oxy)-5-(((tert-butyldiphenylsilyl)oxy)methyl)-3-fluorotetrahydrothiophen-2-yl)-1,3,5-triazin-2 (1H)-one (12) (12.2 g, 16.51 mmol) was dissolved in methanol (anhydrous) (110 mL, 16.51 mmol) in a 200 mL one-neck round bottom flask under nitrogen. The solution was treated with ammonium fluoride (5.20 g, 140 mmol) and was stirred at 60° C. Thin-layer chromatography (30% MeOH/DCM) after 2 h @ 60° C. showed complete consumption of starting material. The mixture was warmed to 60° C. for a total of 3 h. Reaction was cooled to room temperature, was combined with 12 g silica gel (230-400 mesh), and the mixture was concentrated to dryness. The crude plug was eluted over a 25 G UltraSil® SNAP® cartridge with a 5-25% MeOH/DCM gradient into 27 mL fractions. Fractions 12-66 were combined and concentrated to afford 4.8 g of a white solid. The solid was triturated with 20 mL absolute EtOH for 1 h and the white solid was collected, washed with MeOH followed by diethyl ether and was dried on the filter overnight to afford 2.40 g (55%) of the title compound (1) as a fine white solid. The mother liquor was concentrated in vacuo to give 2.05 g of a white foam that appeared to contain primarily the decomposition product of the title compound by TLC and LCMS. This residue was dissolved in MeOH, was treated with 10 mL Florisil® adsorbent (60-100 mesh, Sigma Aldrich), and was concentrated to dryness. The plug was chromatographed over a 25 G UltraSil® SNAP® cartridge, eluting with a 5-25% MeOH/DCM gradient into 27 mL fractions. Fractions 15-22 were combined and concentrated to give 360 mg of a white foam. Crystallization of the foam from MeCN afforded an additional 264 mg (6%) of the title compound (1) as a fine white solid.

$^1$H NMR (400 MHz, DMSO-$d_6$) δ 8.74 (d, J=1.3 Hz, 1H), 7.64-7.57 (m, 2H), 6.23 (dd, J=11.5, 5.4 Hz, 1H), 5.89 (d, J=5.2 Hz, 1H), 5.31 (t, J=5.2 Hz, 1H), 4.96 (dt, J=50.7, 5.9 Hz, 1H), 4.22 (dq, J=11.5, 5.7 Hz, 1H), 3.71-3.55 (m, 2H), 3.17 (q, J=5.5 Hz, 1H).

$^{13}$C NMR (101 MHz, DMSO-$d_6$) δ 165.88, 158.08, 158.05, 153.65, 96.78, 94.86, 73.42, 73.19, 61.26, 57.43, 57.26, 51.94, 51.90 ppm.

$^{19}$F NMR (376 MHz, DMSO-$d_6$) δ −192.77 (dt, J=50.8, 11.7 Hz).

LC/MS: [M+H]=263.1, 98.2% purity.

Example 2

NCI60 Human Tumor Cell Line Anticancer Drug Screen

Embodiments of the disclosed compounds may be screened for anticancer activity using the NCI60 human tumor cell line anticancer drug screen (see, e.g., Shoemaker, Nature Reviews Cancer 2006, 6:813-823; https://dtp.cancer.gov/discovery_development/nci-60/handling.htm).

Standard Operating Procedures for Sample Preparation:

General: NCI60 testing is performed in two parts: first a single concentration is tested in all 60 cell lines at a single dose of $10^{-5}$ molar or 15 μg/ml. If the results obtained meet selection criteria, then the compound is tested again in all 60 cell lines in 5×10 fold dilutions with the top dose being $10^{-4}$ molar or 150 μg/ml. Compounds accepted for NCI60 testing are prepared for both 1-dose and 5-dose testing at the same time.

Agents Received: Synthetics and pure compounds with known molecular weight and macromolecules and compounds without molecular weights—Aliquots of agents identified for testing are weighed and transferred into pre-weighed glass vials. Compounds are solubilized in these vials. Except when specifically noted, all agents are stored in a −70° C. freezer. Crude Natural Products—crude natural product extracts are plated on detachable polypropylene (PP) 96-well microtiter plates. Plates are dried and stored at −20° C. until called up for 1-dose testing. Based on the results of the 1-dose testing, those samples selected for 5-dose testing are rearranged from 88 wells to 72 wells per 96 well plate with a column of standard agent, Adriamycin, NSC 123127, and a new platemap is created and uploaded for assignment. Extracts are then solubilized at 40 mg/ml in DMSO or water.

Concentration Requirements—1-dose/cancer in vitro program: DMSO:glycerol 9:1 (unless otherwise noted) at a concentration of 4 mM for the one dose assay and 40 mM for the 5-dose assay. In both cases the solution is diluted 1:400, giving a High Test concentration of 10 or 100 μM respectively. Synthetic agents (macromolecules) without a molecular weight are prepared in DMSO:glycerol 9:1 (unless otherwise noted) at a concentration of 6 and 60 mg/ml which is diluted 1:400, giving a High Test concentration of 15 and 150 μg/ml. Natural products crude extracts which are organic solvent soluble are prepared in DMSO, while those which were produced by aqueous extraction are solubilized in water, both at 40 mg/ml.

Volume Requirements—prescreen/cancer in vitro program: The cancer screen requires 100 μl for 1 log, 5-dose dilutions of regular compounds and 75 μl for 1-dose testing. 1-dose testing is done at ⅒th the high concentration of 5-dose testing, so the volume requirement is 210 μl+20% at 40 mM for compounds with molecular weights or 210 μl+20% at 60,000 μg/ml=250 μl for compounds without molecular weights (macromolecules) (i.e. less than 10 mg for MW=1000 or 15 mg for compounds tested as weight/volume).

Compound Special Instructions: Special instructions, (e.g. oxygen sensitive, light sensitive) can change the handling of the agent according to the instructions.

Fresh Compounds: Compounds that are identified as needing to be prepared fresh before use are solubilized no more than one hour before serial dilution. It is serial diluted on a TECAN Freedom 200 (two drugs/plate), transferred to a column plate and stored under nitrogen in a desiccator box until delivered to the testing lab.

Solubilization Standard Operating Procedures

Entering Information into the NPSG TECAN System: Prior to beginning the solubilization procedure, information is entered into the NPSG TECAN (Visual Basic instrument control and front end to ORACLE) system for each compound to be solubilized by the TECAN Freedom 200. A set of 72 compounds are assigned to a plateset by entering the shiplist numbers. A shiplist is loaded into TECAN software which looks up quantity and MW (from DIS Oracle tables) and calculates volume of solvent to be added to each vial to get constant concentration (40 mM or 60,000 μg/ml) and adjusts concentrations if insufficient material for 1-dose and a test & one retest (75 μl @ 4 mM & 200 μl @ 40 mM+20% or 75 μl @ 6,000 μg/ml & 200 μl @ 60,000 μg/ml+20%). A Platemap (defines which compound is in which well) for prescreen is uploaded via ORADIS to ORACLE PLATE-WELL table.

Supplies and Equipment: Vials are put on the TECAN table in shiplist order as designated on the PLATEMAP printout. TECAN Freedom robot adds appropriate volume of solvent (methanol/ethyl acetate/methyl-t-butyl ether, 6:3:1) to each vial to give constant concentration. Technician inspects each vial individually and sonicates, warms, etc. to achieve solution keeping the time of exposure less than two hours. Plate Preparation prior to drug solution transfer: Technician prepares three 96 well PP detachable well plates (one for 1-dose and two for 60 cell testing): 100 μl of 10% glycerol in isopropanol is added to each well. [After drug solution addition and vacuum drying, this leaves 10 μL glycerol per well.]

TECAN mixes drug solution in vial once then transfers 40 μL (400 μM) of drug solution into each well of the 96 well detachable plate for 1-dose and 400 μL (4,000 μM) into 96 well PP detachable well plates for full 60 cell screen. All plates are transferred to the SpeedVac system for drying. All solvent is removed by high vacuum without heating leaving a residue of glycerol plus drug in bottom of the well. Dry plates are stored @ −70° C. until called for test, typically 1-3 weeks. Untransferred residue in glass vials is dried in a SpeedVac and stored dry at −70° C. and can be used if additional retesting is required.

For 1-dose 60 cell testing: On the day of or the day before drug addition to growing cells in tissue culture, a strip of standards (adriamycin, NSC 123127 prepared and stored the same as the compounds) is added to the detachable well plate, and 90 μl DMSO is added to each well (4 mM solution), and mixed/sonicated and 75 μl is transferred, using a 12 channel hand pipettor, to a 12 channel reservoir plates (column plates), which is sealed and stored under nitrogen in a desiccator box until delivered to testing lab. The labels are placed at the right and the left of the front of the reservoir plate. It will be the first and the last NSC number in the row. Rows are transferred from detachable plate to columns 3-12 of column plates. Plates are sealed and stored under nitrogen no more than 24 hours prior to drug addition.

For 5-dose 60 cell testing: On the day of drug addition to growing cells in tissue culture, 90 μl DMSO is added to each well (40 mM solution), and mixed/sonicated on the shaker of the TECAN Freedom 200. Tubes are then placed on a TECAN Freedom 200 (two drugs/plate), and serial diluted/transferred to column plates which is sealed and stored under nitrogen in a desiccator box until delivered to testing lab. The plate labels are printed by the SATO thermal transfer printer utilizing the ORACLE front end program option AA—Expid NSC labels. The labels are placed at the right and the left of the front of the reservoir plate, drug one by column one and drug two by column twelve.

Vehicle Selection—Synthetics: The vehicles of choice are DMSO and water. Most agents are solubilized using one of these two vehicles. Other vehicles are used at the request of the supplier or based upon past testing methods. Agents utilizing volatile solvents as a vehicle are labeled 'Fresh' and are prepared within an hour of screening addition. Currently, all synthetic agents for Prescreen/Cancer screening are prepared in DMSO:glycerol 9:1, unless another vehicle is indicated. When water is indicated, the compound is solubilized in either distilled water or in cell culture media (RPMI 1640) without serum. All solubilizations requiring THF, ethanol, methanol, or other volatile solvents are prepared fresh to reduce evaporation.

Minimum Volume Requirements: The goal of solubilization is to deliver the highest requested concentration of an agent for the screening process. However, the number of vials required by the program screening the agent determines the minimum amount of vehicle that can be added. If the amount of material is insufficient to create the required number of aliquots, the concentration is dropped to ensure an appropriate volume is met.

Volume Requirements—1-dose/cancer in vitro program: The cancer screen requires 100 μl for 1 log, 5-dose dilutions for the regular compounds. For compounds solubilized on the TECAN for both 1-dose and five-dose cancer assays, a minimum volume of 250 μl is needed, enough for the initial 1-dose assay, a test and a retest in the 5-dose assay.

Solubility Codes: The agents will not always solubilize to a clear solution absent of particles. Therefore the solution is described via a code best describing the solubility of the agent in the vehicle. It is the clarity of the solution that is being evaluated. Presence or absence of color is not accounted for in the solubility codes.

NCI60 Screening Methodology

NCI60 Cell One-Dose Screen:

General Description: All compounds submitted to the NCI 60 Cell screen are tested initially at a single high dose ($10^{-5}$ M) in the full NCI 60 cell panel. Only compounds which satisfy pre-determined threshold inhibition criteria in a minimum number of cell lines will progress to the full 5-dose assay. The threshold inhibition criteria for progression to the 5-dose screen was selected to efficiently capture compounds with anti-proliferative activity based on careful analysis of historical DTP screening data. The threshold criteria may be updated as additional data becomes available.

Interpretation of One-Dose Data: The One-dose data will be reported as a mean graph of the percent growth of treated cells and will be similar in appearance to mean graphs from the 5-dose assay. The number reported for the One-dose assay is growth relative to the no-drug control, and relative to the time zero number of cells. This allows detection of both growth inhibition (values between 0 and 100) and lethality (values less than 0). This is the same as for the 5-dose assay, described below. For example, a value of 100 means no growth inhibition. A value of 40 would mean 60% growth inhibition. A value of 0 means no net growth over the course of the experiment. A value of −40 would mean 40% lethality. A value of −100 means all cells are dead. Information from the One-dose mean graph is available for COMPARE analysis.

NCI60 Cell Five-Dose Screen:

Compounds which exhibit significant growth inhibition in the One-Dose Screen are evaluated against the 60 cell panel at five concentration levels.

The human tumor cell lines of the cancer screening panel are grown in RPMI 1640 medium containing 5% fetal bovine serum and 2 mM L-glutamine. For a typical screening experiment, cells are inoculated into 96 well microtiter plates in 100 μL at plating densities ranging from 5,000 to 40,000 cells/well depending on the doubling time of individual cell lines. After cell inoculation, the microtiter plates are incubated at 37° C., 5% $CO_2$, 95% air and 100% relative humidity for 24 h prior to addition of experimental drugs.

After 24 h, two plates of each cell line are fixed in situ with TCA, to represent a measurement of the cell population for each cell line at the time of drug addition (Tz). Experimental drugs are solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 μg/ml gentamicin. Additional four, 10-fold or ½ log serial dilutions are made to provide a total of five drug concentrations plus control. Aliquots of 100 μL of these different drug dilutions are added to the appropriate microtiter wells already containing 100 μL of medium, resulting in the required final drug concentrations.

Following drug addition, the plates are incubated for an additional 48 h at 37° C., 5% $CO_2$, 95% air, and 100% relative humidity. For adherent cells, the assay is terminated by the addition of cold TCA. Cells are fixed in situ by the gentle addition of 50 μL of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 μL) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM Trizma® base (Tris base), and the absorbance is read on an automated plate reader at a wavelength of 515 nm. For suspension cells, the methodology is the same except that the assay is terminated by fixing settled cells at the bottom of the wells by gently adding 50 μL of 80% TCA (final concentration, 16% TCA). Using the seven absorbance measurements [time zero, (Tz), control growth, (C), and test growth in the presence of drug at the five concentration levels (Ti)], the percentage growth is calculated at each of the drug concentrations levels. Percentage growth inhibition is calculated as:

$[(Ti-Tz)/(C-Tz)] \times 100$ for concentrations for which $Ti >/= Tz$ $[(Ti-Tz)/Tz] \times 100$ for concentrations for which $Ti < Tz$ 50% (GI50) is calculated from $[(Ti-Tz)/(C-Tz)] \times 100=50$, which is the drug concentration resulting in a 50% reduction in the net protein increase (as measured by SRB staining) in control cells during the drug incubation. The drug concentration resulting in total growth inhibition (TGI) is calculated from Ti=Tz. The LC50 (concentration of drug resulting in a 50% reduction in the measured protein at the end of the drug treatment as compared to that at the beginning) indicating a net loss of cells following treatment is calculated from $[(Ti-Tz)/Tz] \times 100=-50$. Values are calculated for each of these three parameters if the level of activity is reached; however, if the effect is not reached or is exceeded, the value for that parameter is expressed as greater or less than the maximum or minimum concentration tested.

Figure 3A:
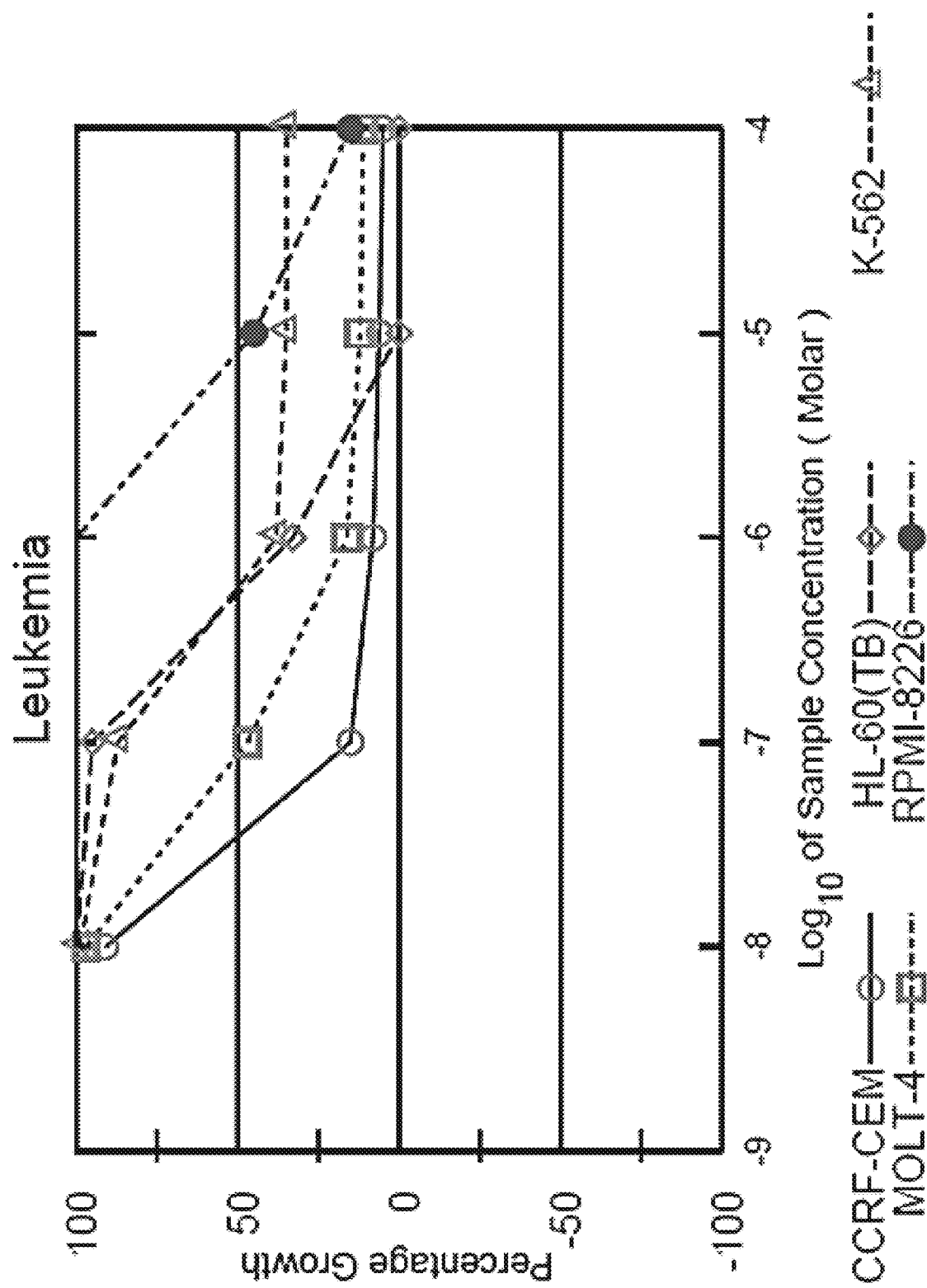
FIGS. 3A and 3B show GI50 (drug concentration resulting in a 50% reduction in net protein increase) data for Compound 1 and 5-aza-T-dCyd, respectively, against leukemia cell lines.
Figure 3B:
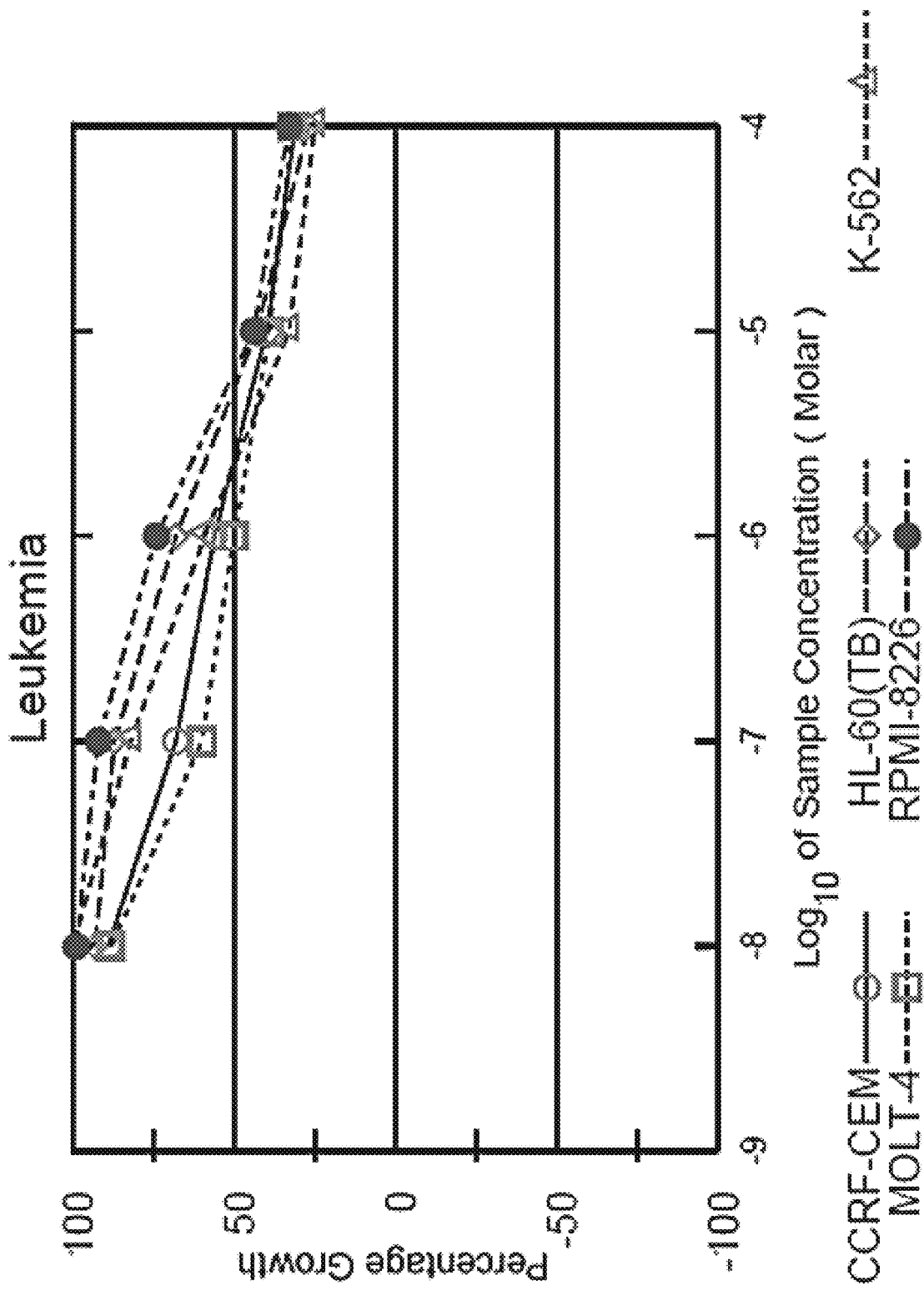
Figure 4A:
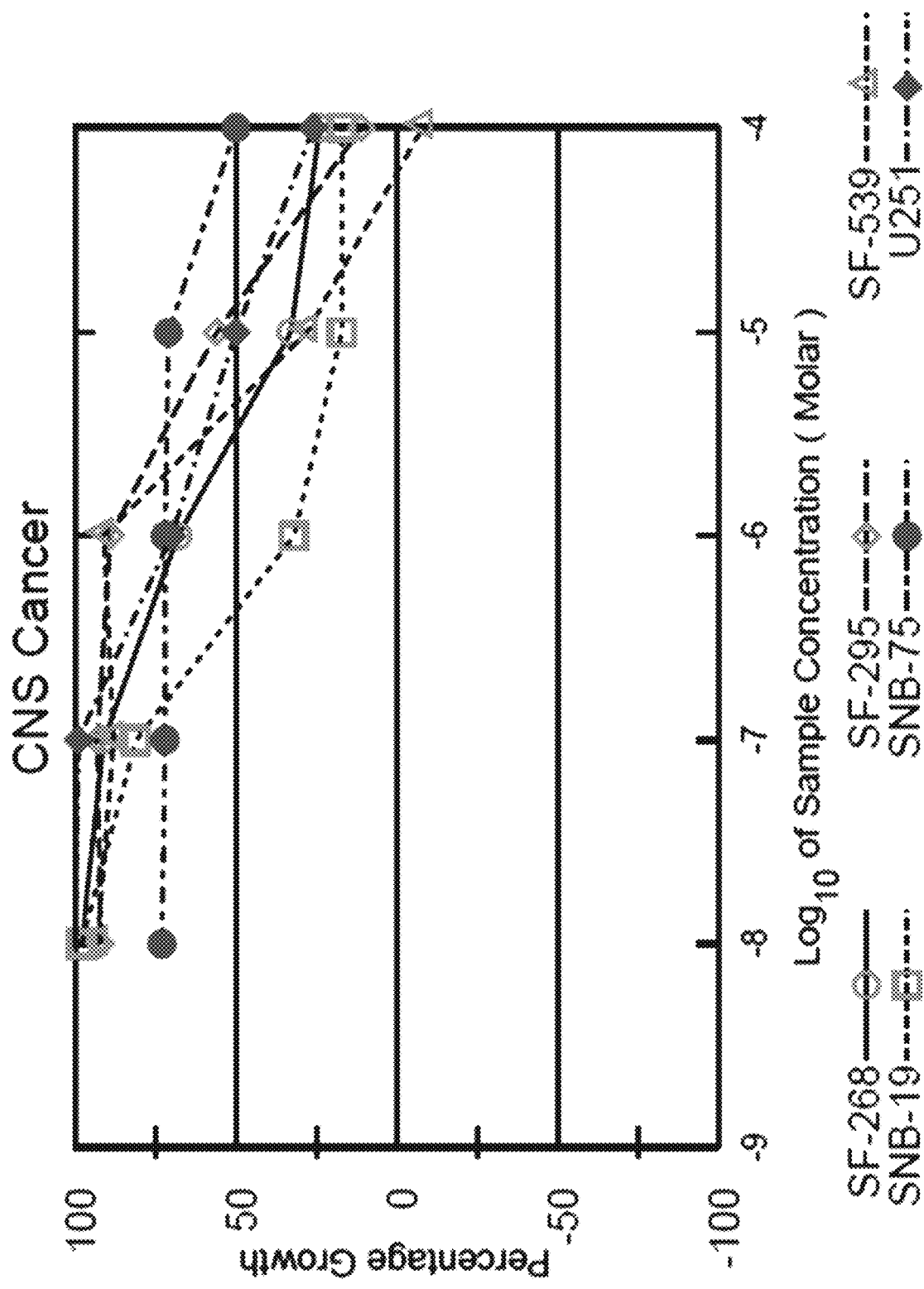
FIGS. 4A and 4B show GI50 data for Compound 1 and 5-aza-T-dCyd, respectively, against central nervous system (CNS) cancer cell lines.
Figure 4B:
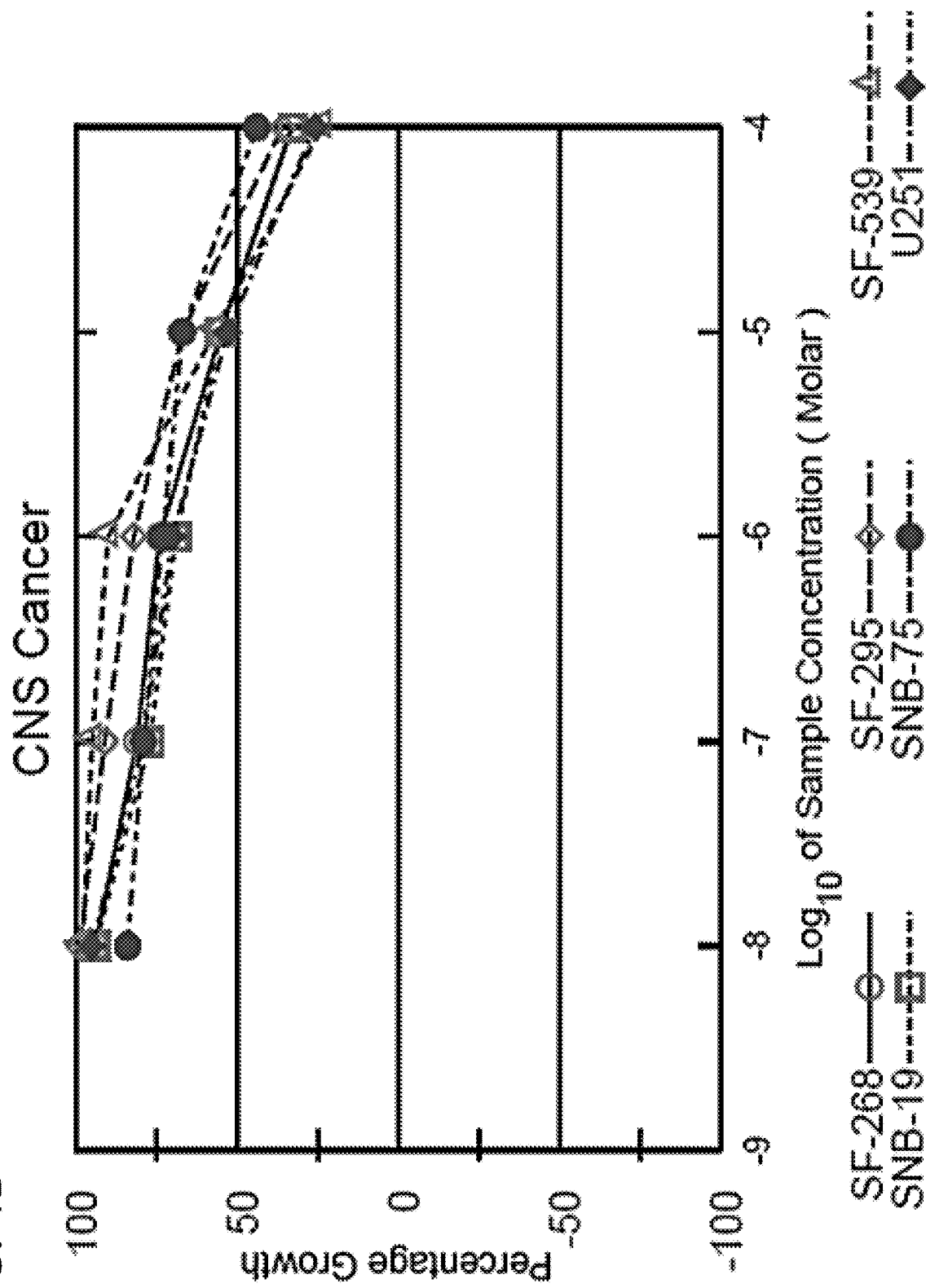
Figure 5A:
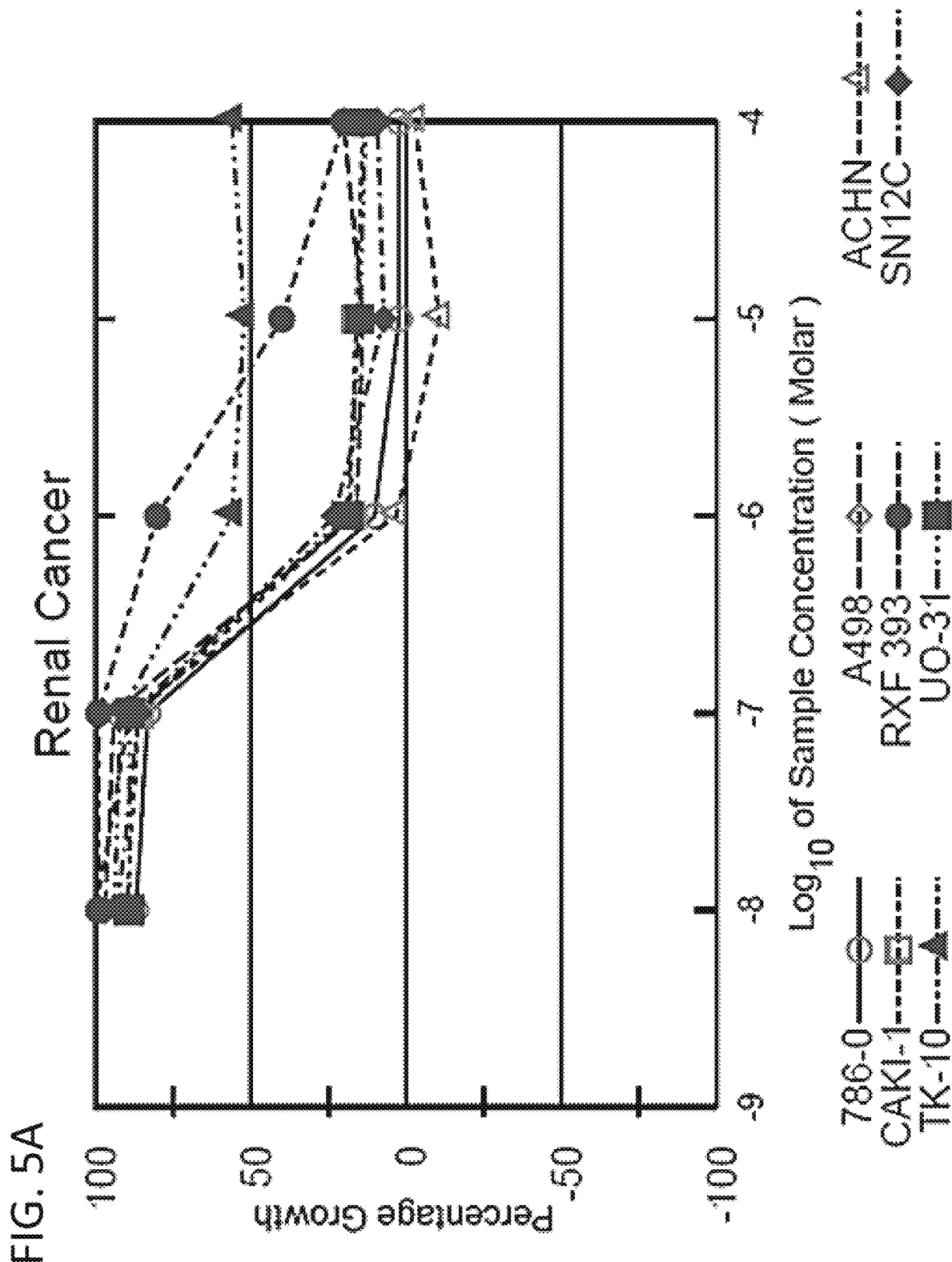
FIGS. 5A and 5B show GI50 data for Compound 1 and 5-aza-T-dCyd, respectively, against renal cancer cell lines.
Figure 5B:
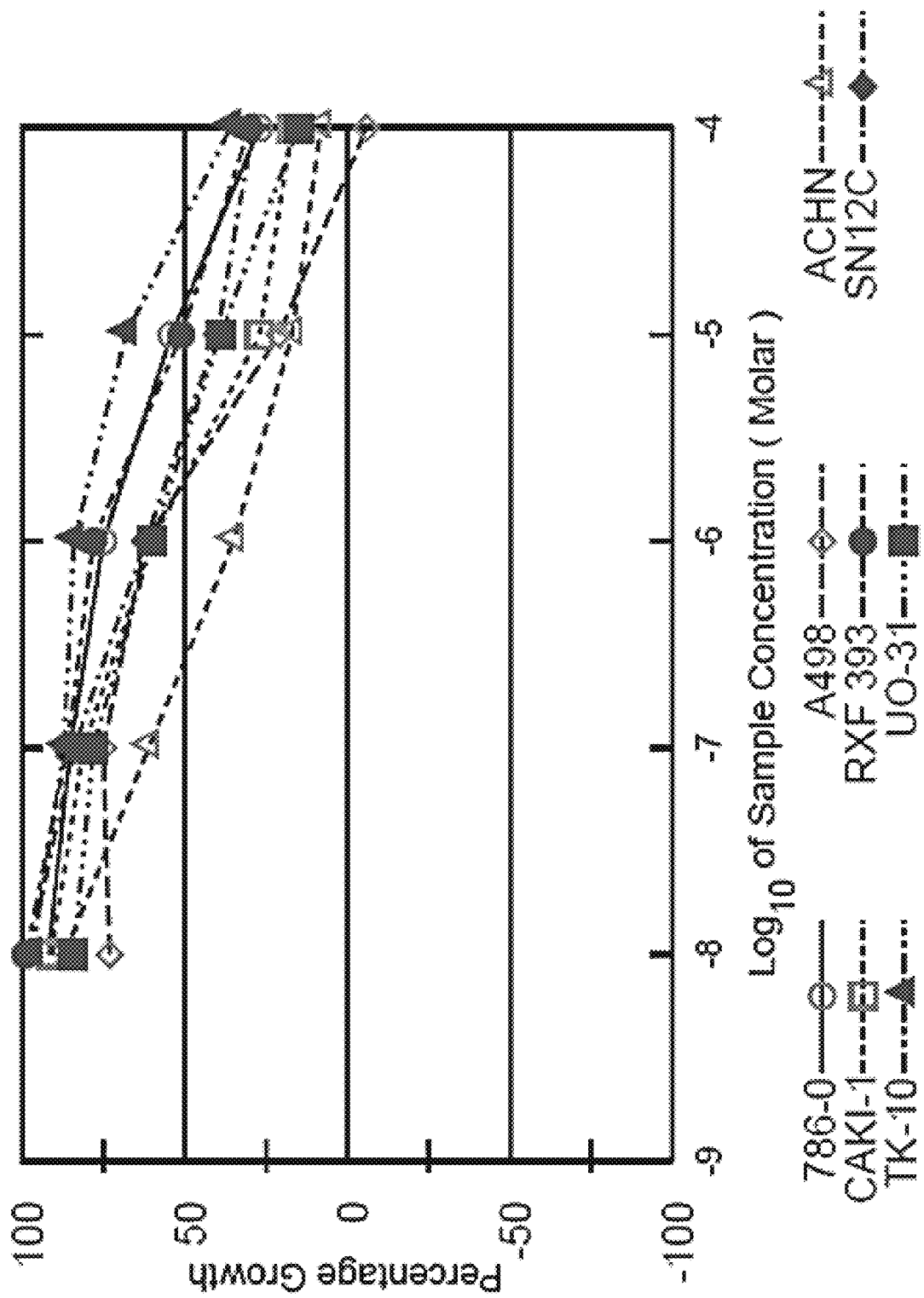
Figure 6B:
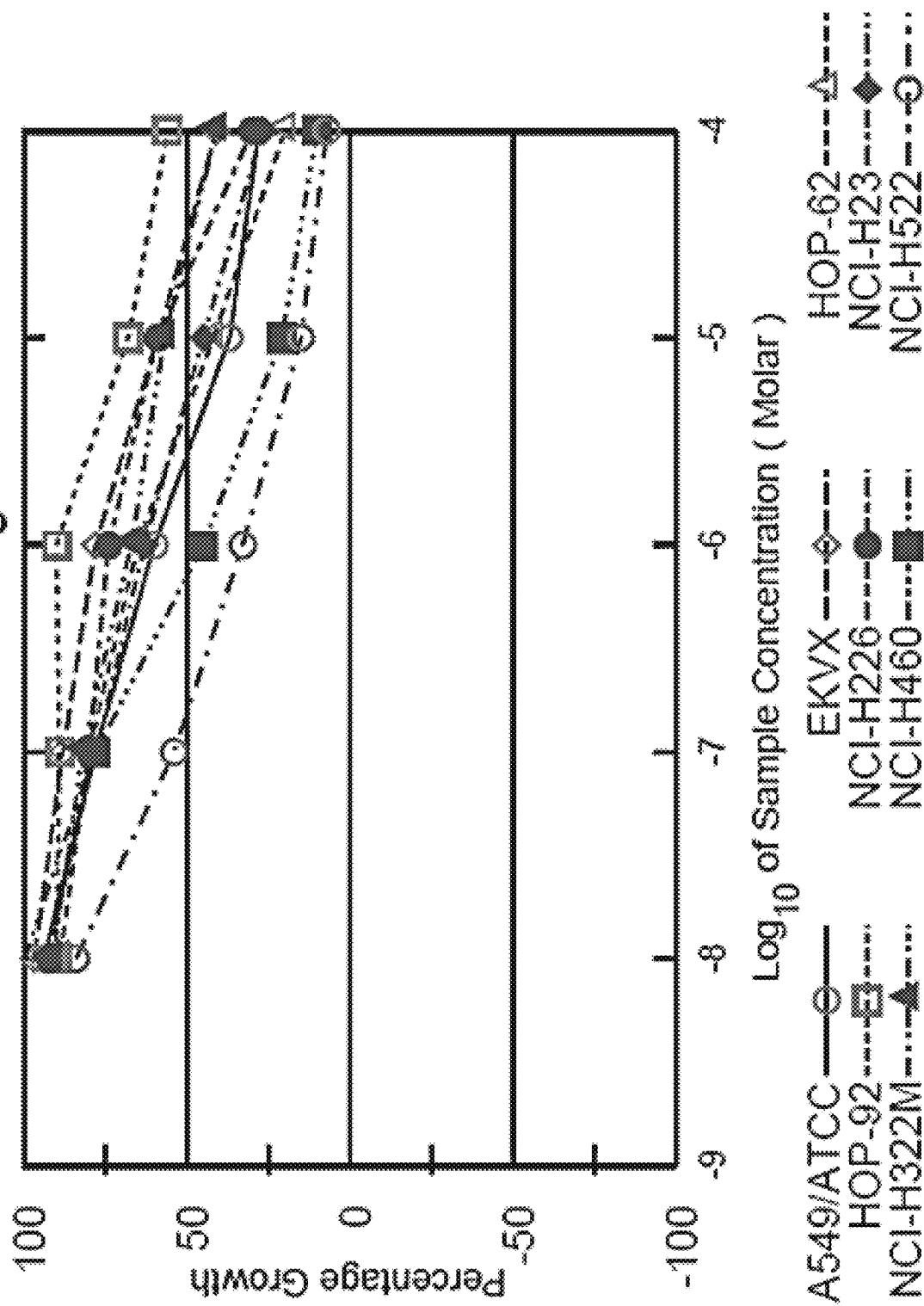
Figure 7A:
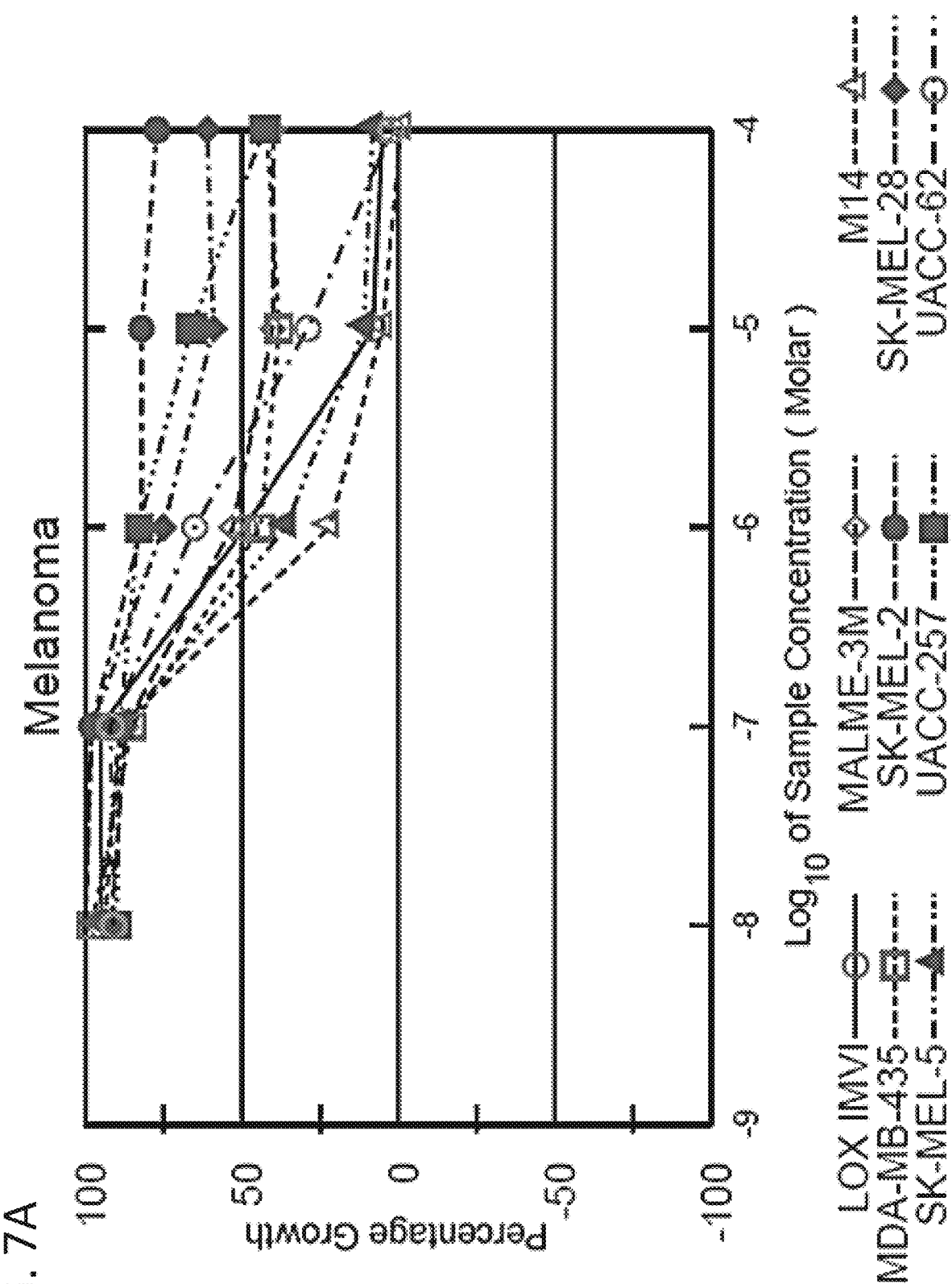
FIGS. 7A and 7B show GI50 data for Compound 1 and 5-aza-T-dCyd, respectively, against melanoma cell lines.
Figure 7B:
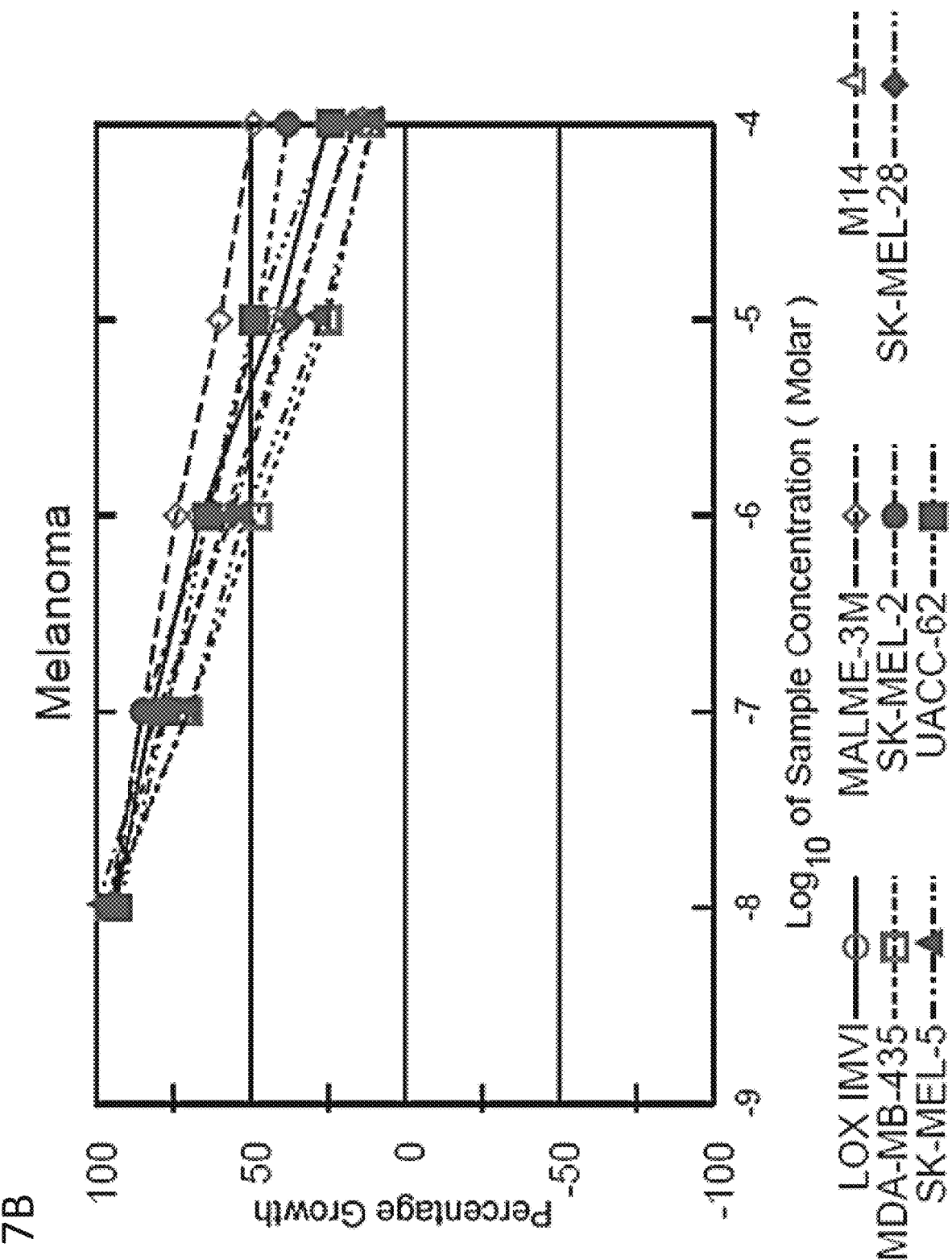
Figure 8A:
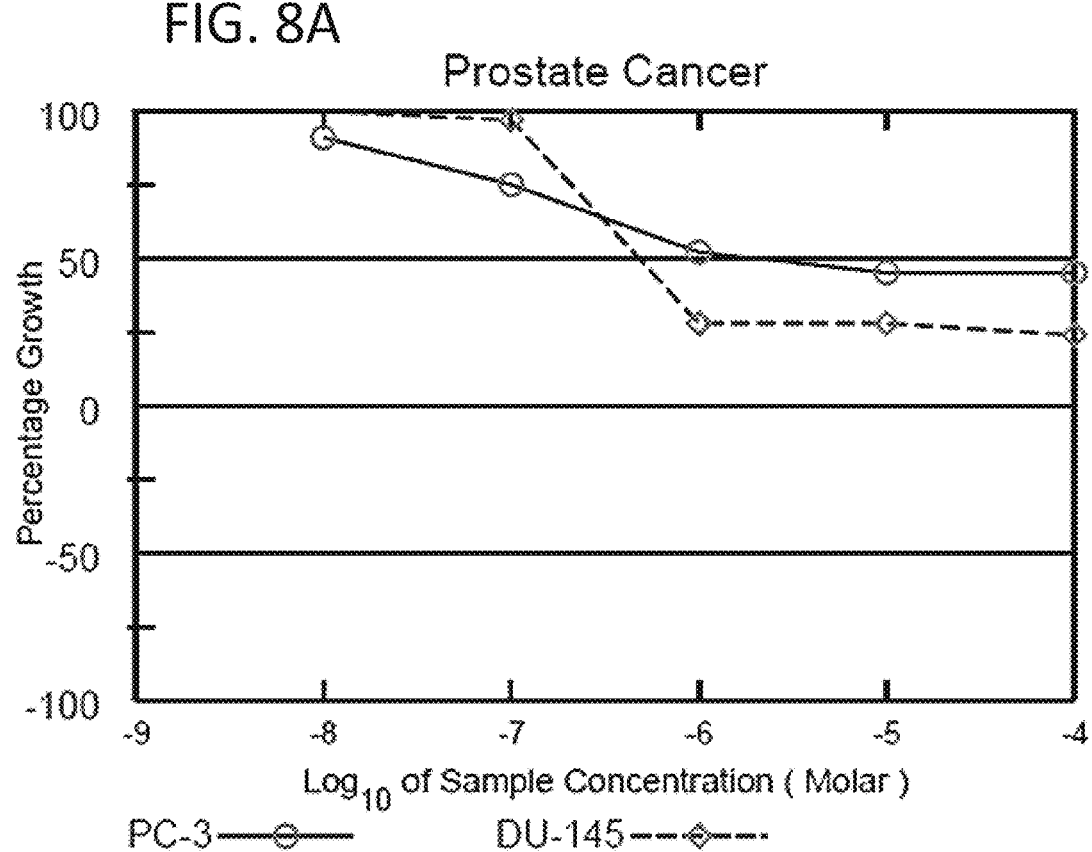
FIGS. 8A and 8B show GI50 data for Compound 1 and 5-aza-T-dCyd, respectively, against prostate cancer cell lines.
Figure 8B:
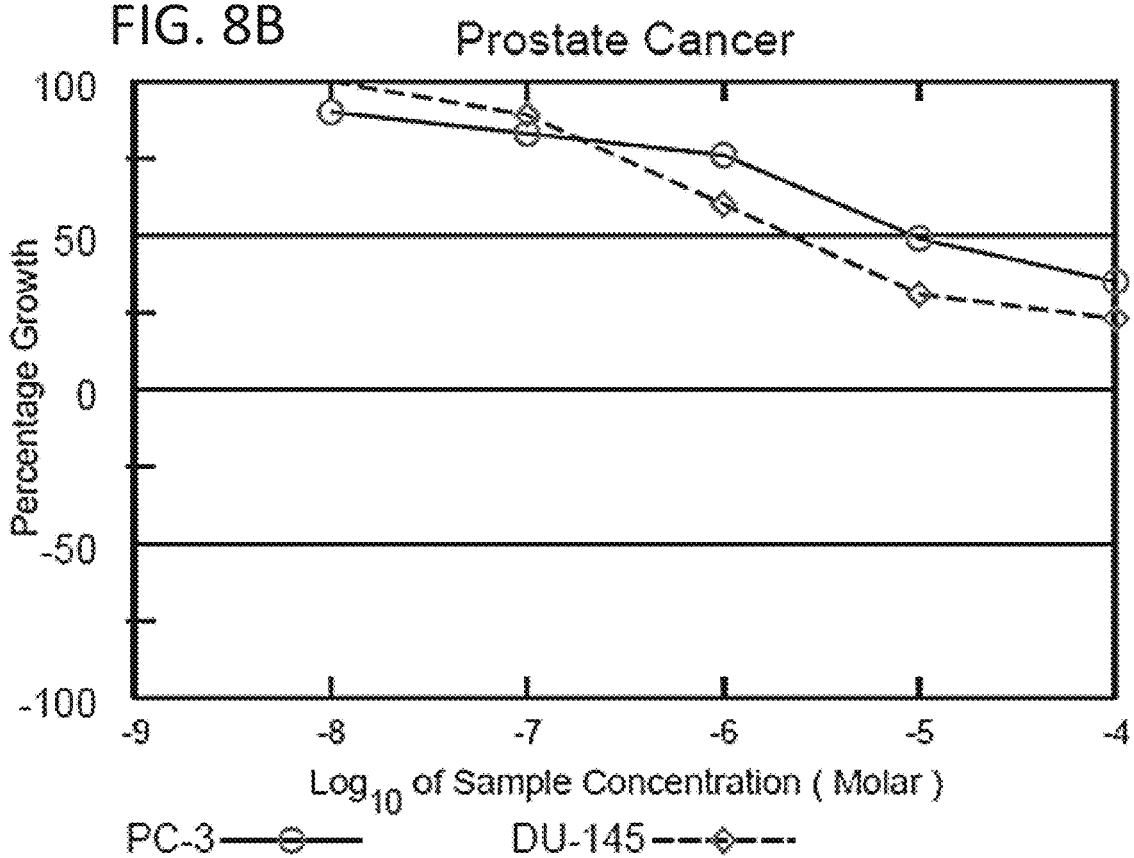
Figure 9A:
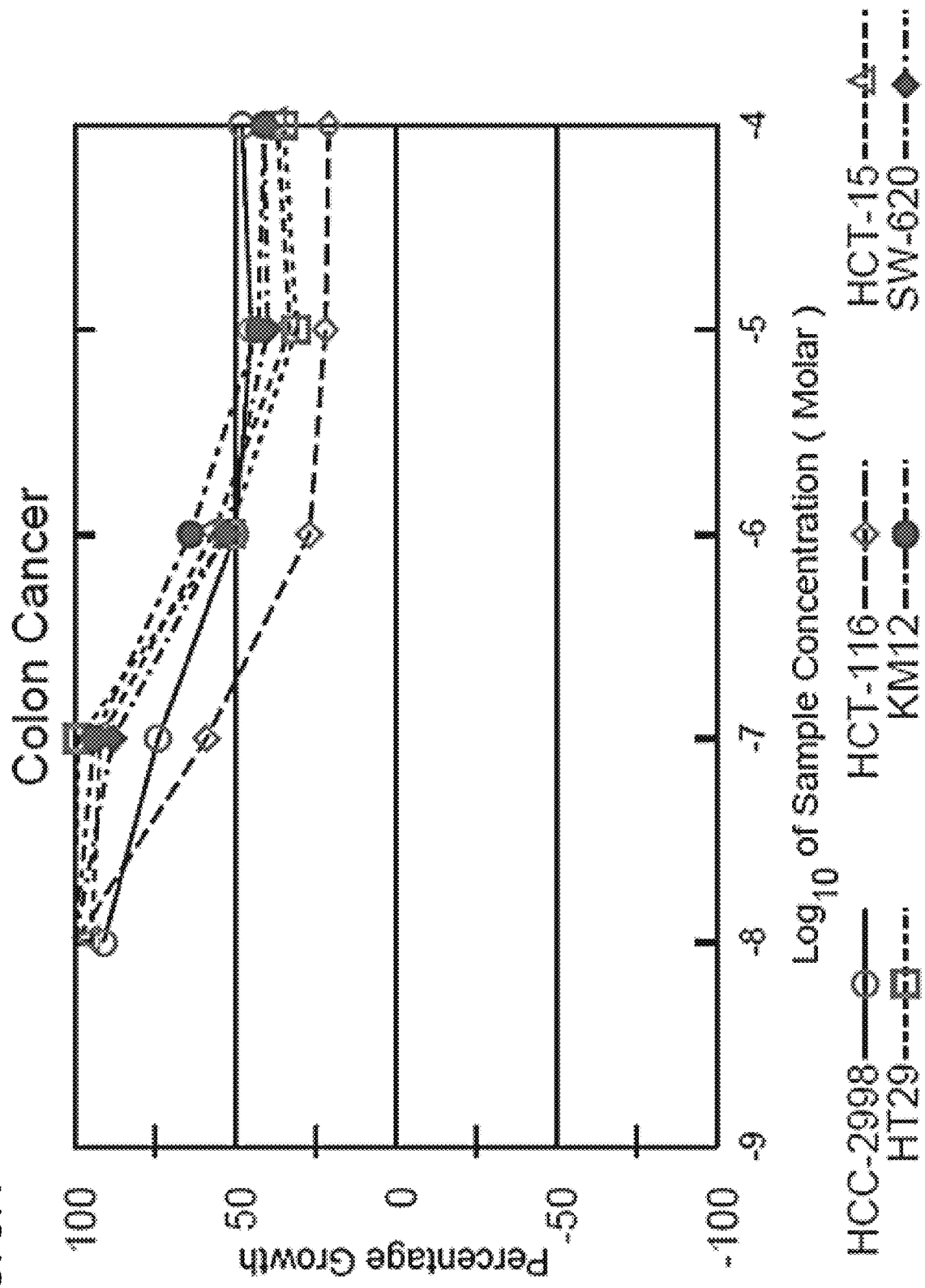
FIGS. 9A and 9B show GI50 data for Compound 1 and 5-aza-T-dCyd, respectively, against colon cancer cell lines.
Figure 9B:
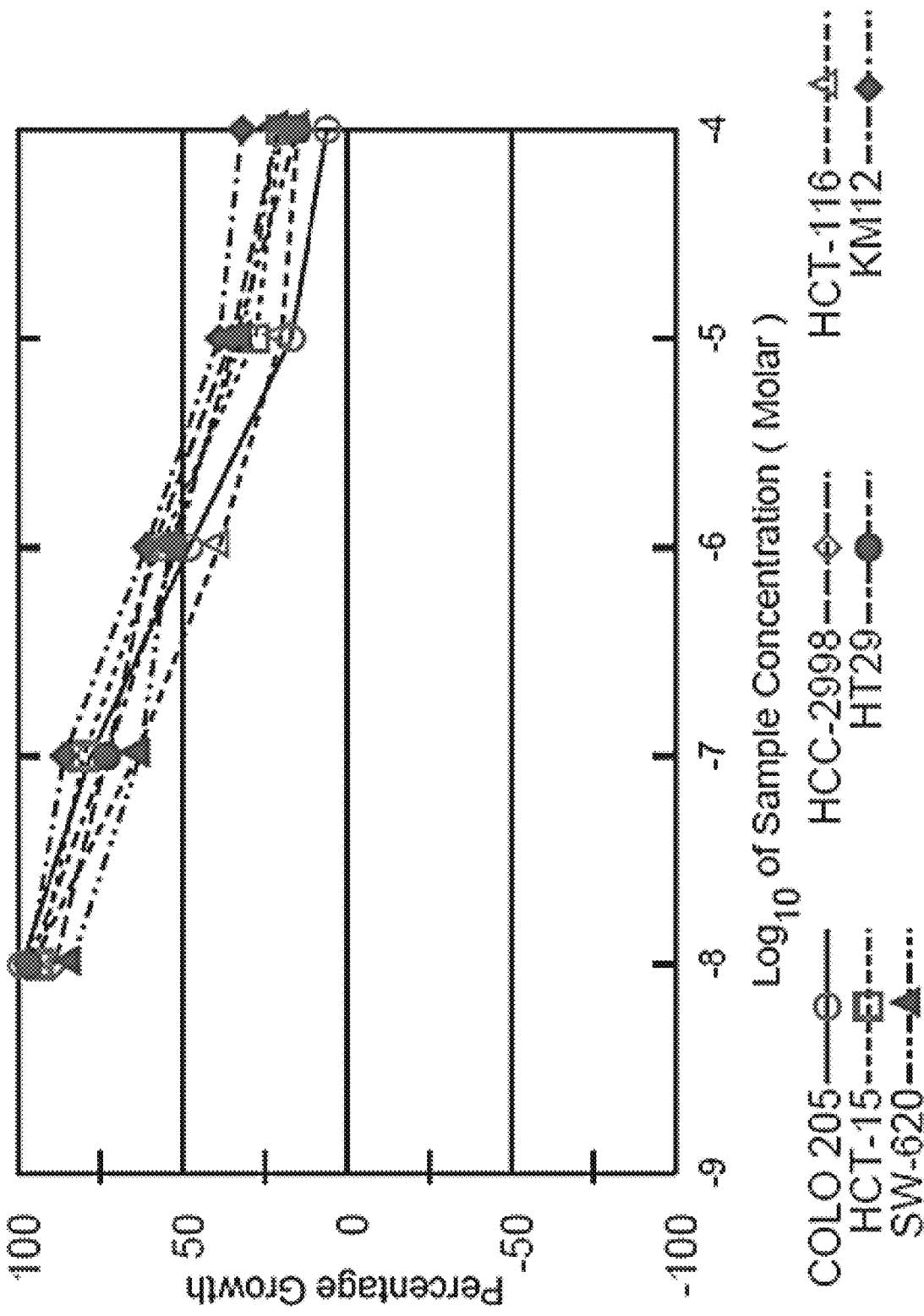
Figure 10A:
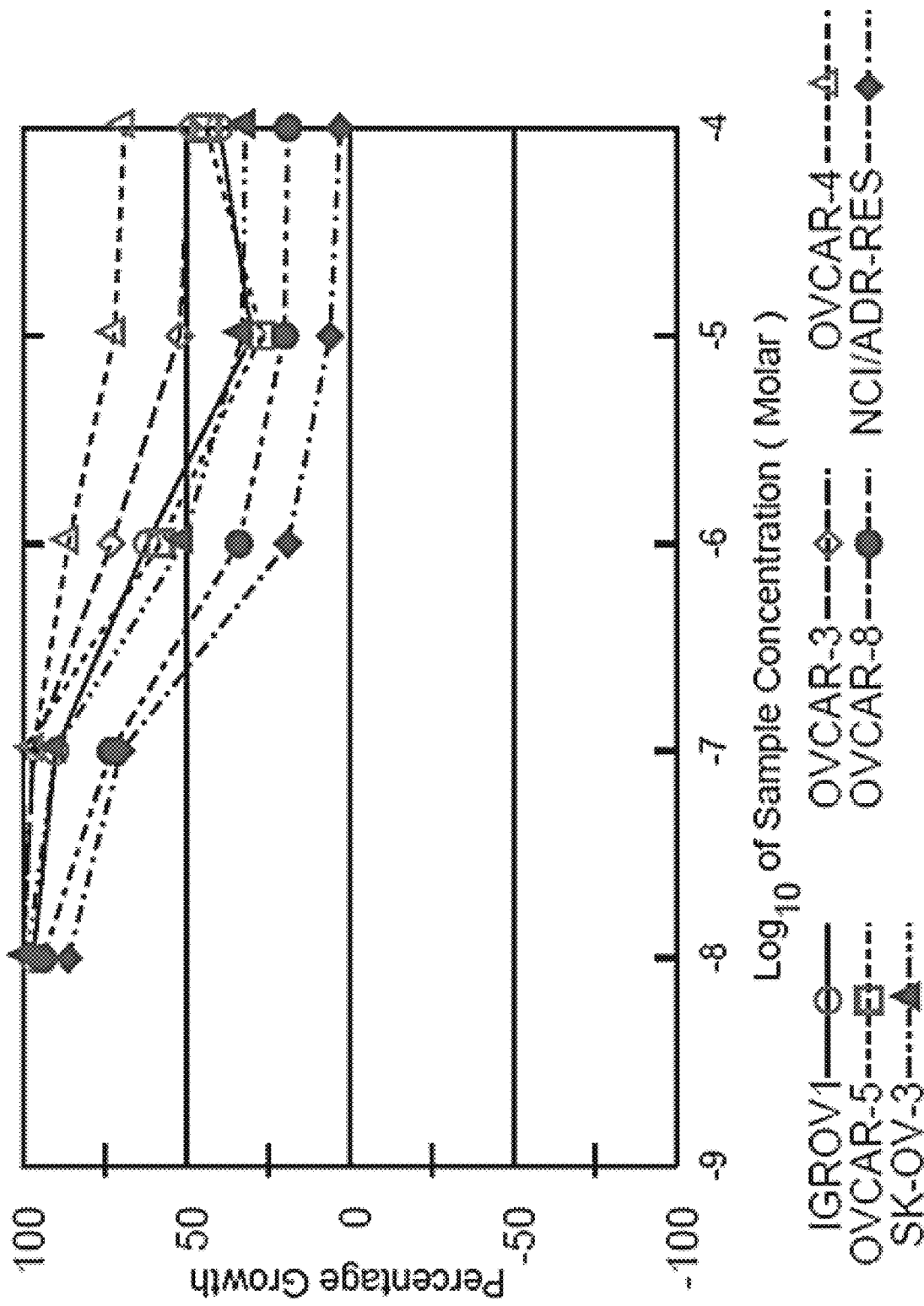
FIGS. 10A and 10B show GI50 data for Compound 1 and 5-aza-T-dCyd, respectively, against ovarian cancer cell lines.
Figure 10B:
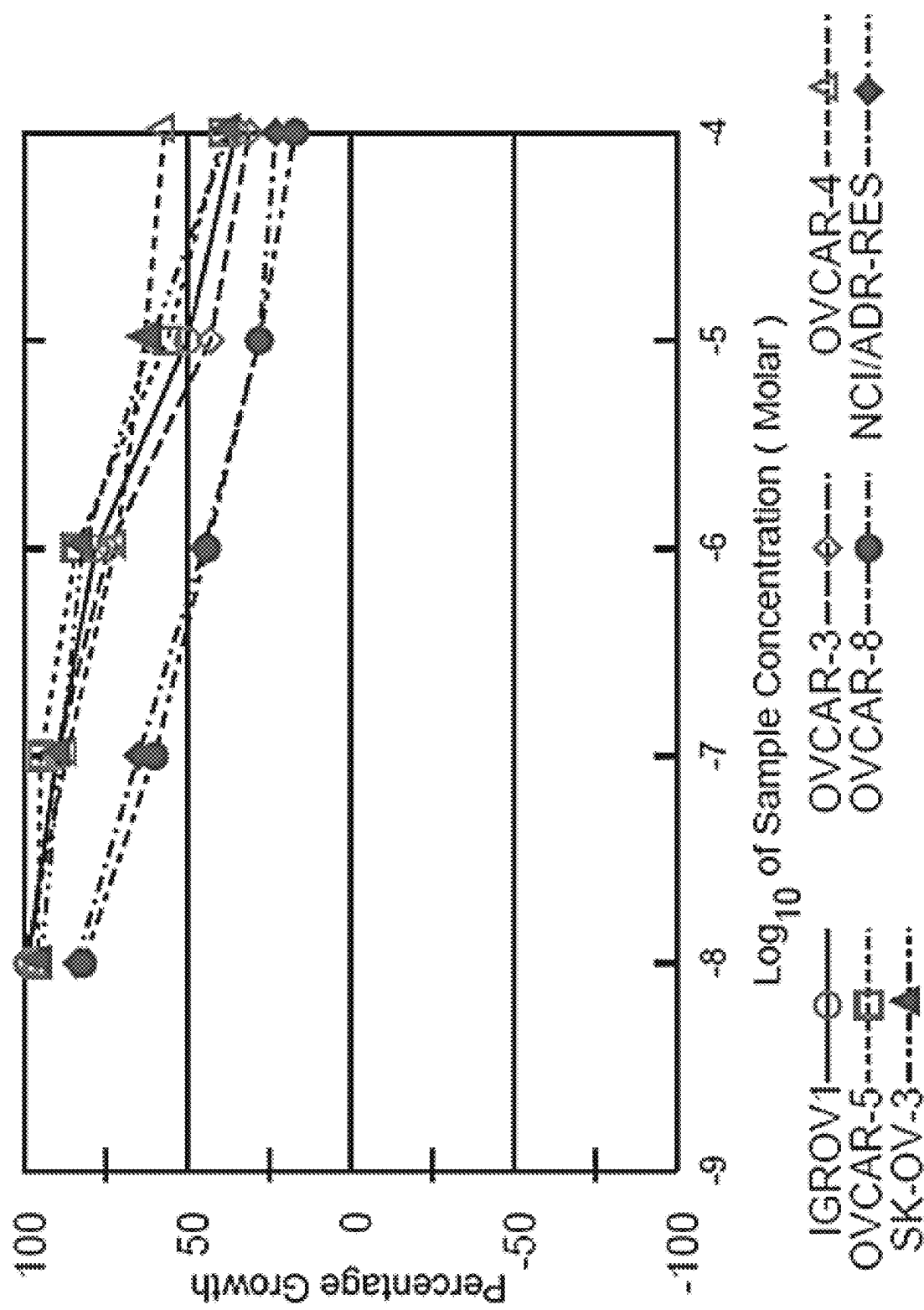
Figure 11A:
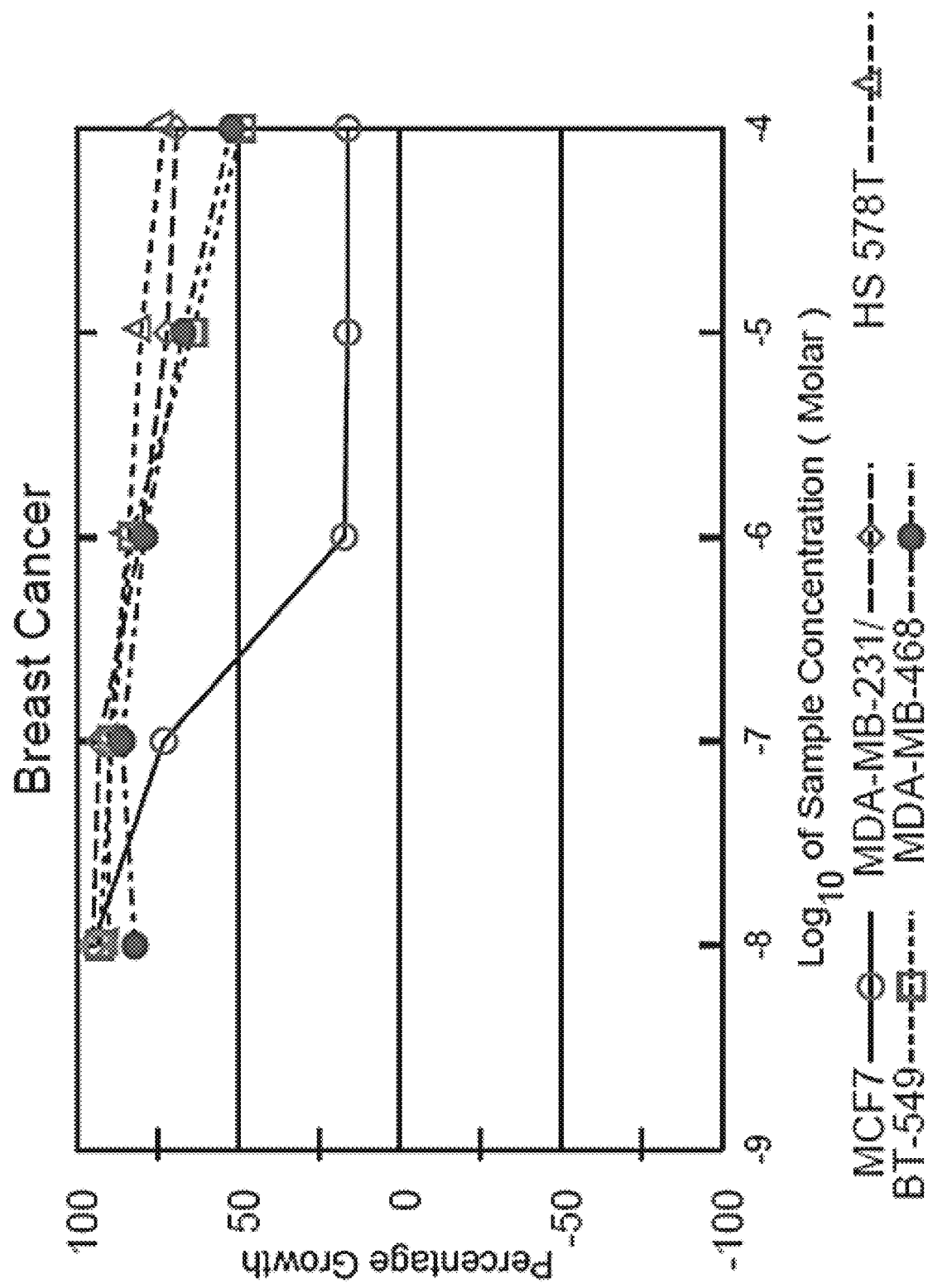
FIGS. 11A and 11B show GI50 data for Compound 1 and 5-aza-T-dCyd, respectively, against breast cancer cell lines.
Figure 11B:
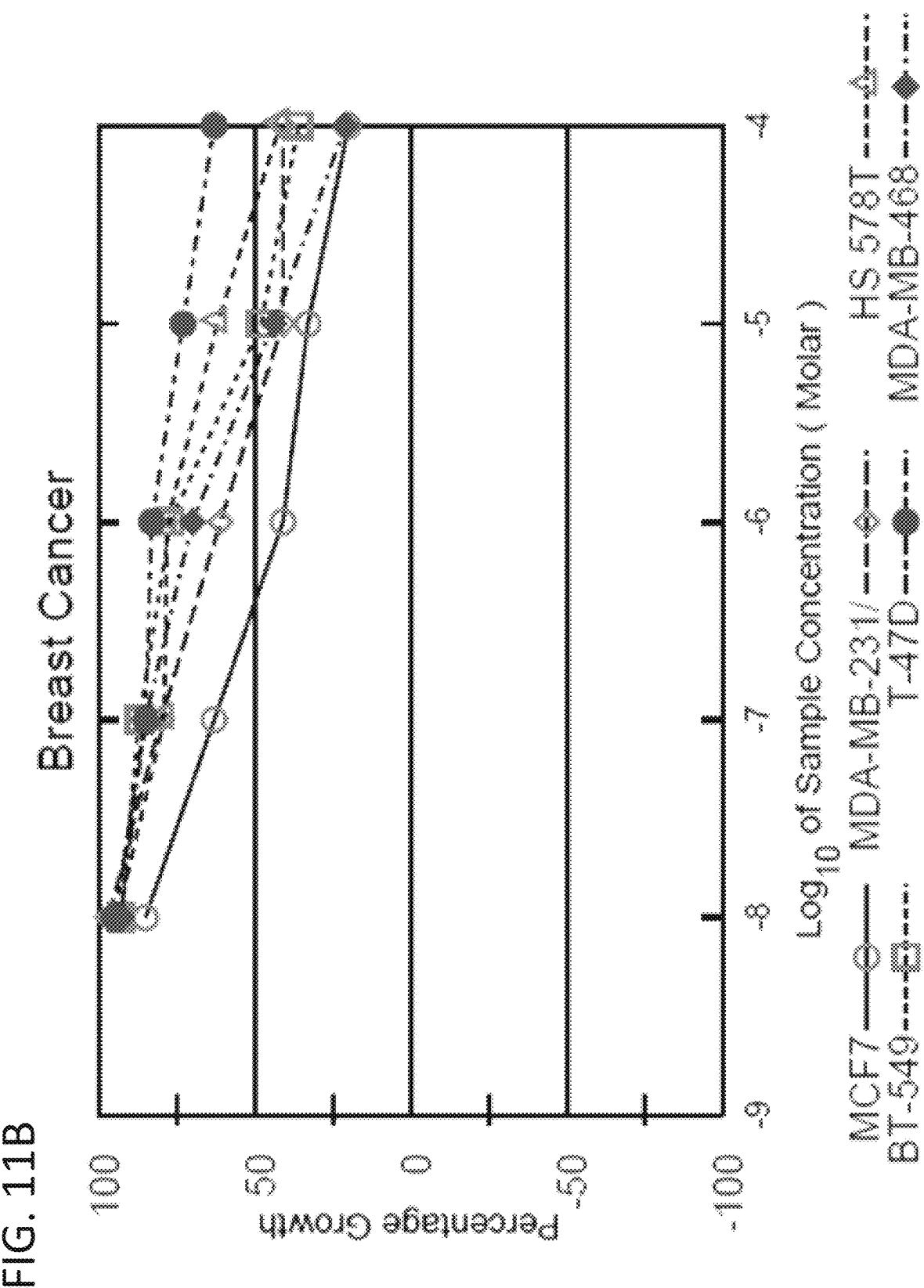

FIGS. 3A-3B show GI50 data for Compound 1 (4-amino-1-(2R,3S,4S,5R)-3-fluoro-4-hydroxy-5-(hydroxymethyl) tetrahydrothiophen-2-yl)-1,3,5-triazin-2(1H)-one) and 5-aza-T-dCyd, respectively, against leukemia cell lines. FIGS. 4A and 4B show GI50 data for Compound 1 and 5-aza-T-dCyd, respectively, against central nervous system (CNS) cancer cell lines. FIGS. 5A and 5B show GI50 data for Compound 1 and 5-aza-T-dCyd, respectively, against renal cancer cell lines. FIGS. 6A and 6B show GI50 data for Compound 1 and 5-aza-T-dCyd, respectively, against non-small cell lung cancer cell lines. FIGS. 7A and 7B show GI50 data for Compound 1 and 5-aza-T-dCyd, respectively, against melanoma cell lines. FIGS. 8A and 8B show GI50 data for Compound 1 and 5-aza-T-dCyd, respectively, against prostate cancer cell lines. FIGS. 9A and 9B show GI50 data for Compound 1 and 5-aza-T-dCyd, respectively, against colon cancer cell lines. FIGS. 10A and 10B show GI50 data for Compound 1 and 5-aza-T-dCyd, respectively, against ovarian cancer cell lines. FIGS. 11A and 11B show GI50 data for Compound 1 and 5-aza-T-dCyd, respectively, against breast cancer cell lines.

Example 3

Xenograft Studies

Xenograft studies were performed in mice with tumors of HCT-116 human colon carcinoma cells, BL0382 human bladder carcinoma cells, OVCAR3 human ovarian carcinoma cells, NCI-H23 NSCLC human lung carcinoma cells, and HL-60 human leukemia cells. Human tumor xenografts were generated in 4- to 6-week-old female athymic nude mice (nu/nu NCr) or NSG mice by subcutaneous injection of tumor cells (HL-60, NCI-H23, OVCAR-3, HCT-116) grown in vitro using RPMI 1640 with 10% fetal bovine serum and 2 mM l-glutamine. For the patient-derived xenograft (PDX) model, BL0382F1232, tumor fragments were serially passaged from donor mice as described for other xenograft models (Plowman et al., "Human tumor xenograft models in NCI drug development." In: Teicher, B. A. (Ed.), *Anticancer Drug Development Guide: Preclinical Screening, Clinical Trials and Approval*. Humana Press, Totowa, N.J., pp. 101-125; 1997). The PDX donor tumors were produced by implantation of tumor material received from human patients into NSG mice. The resulting tumors were serially passaged in NSG mice and fragments were cryopreserved for subsequent establishment of newly tumored animals from the archived material. The mice were housed in an AAALACi (Association for Assessment and Accreditation of Laboratory Animal Care International) accredited facility with food and water provided ad libitum. When tumors reached the predetermined starting weight (staging weight), the animals were randomized into experimental groups and treatment was initiated. Groups included a vehicle control group as well as the drug-treated groups. Drug doses were selected based upon prior experience or newly conducted mouse tolerability studies as described elsewhere (ibid.). Tumors were monitored by bidirectional caliper measurements and the tumor weights were calculated as tumor weight (mg)=(tumor length in mm×tumor width in $mm^2$)/2. Data collection and analysis was performed using the StudyLog software program Study Director (Studylog Systems, Inc., South San Francisco, Calif.).

| Cell Line | Drug | Amount | Route | Schedule |
|---|---|---|---|---|
| HCT-116 | F-aza-TdCyd | 10 mg/kg | IP | QDx5, rest and repeat for 4 cycles* |
| | | 400 mg/kg | IP | Q7Dx3 |
| | F-TdCyd | 240 mg/kg | IV | Q7Dx4 |
| | 5-aza-T-dCyd | 1.5 mg/kg | IP | QDx5, rest and repeat for 4 cycles |
| | gemcitabine | 150 mg/kg | IP | Q7Dx3 |

-continued

| Cell Line | Drug | Amount | | Route | Schedule |
|---|---|---|---|---|---|
| BL0382 | F-aza-TdCyd | 8 | mg/kg | IP | QDx5, rest for 3 cycles |
| | | 250 | mg/kg | IP | Q7Dx3 |
| | | 8 | mg/kg | PO | QDx5, rest for 3 cycles |
| | F-TdCyd | 200 | mg/kg | IV | Q7Dx3 |
| | 5-aza-T-dCyd | 1.5 | mg/kg | IP | QDx5 rest for 3 cycles |
| | gemcitabine | 150 | mg/kg | IP | Q7Dx3 |
| OVCAR3 | F-aza-TdCyd | 8 | mg/kg | IP | QDx5, rest for 3 cycles |
| | | 250 | mg/kg | IP | Q7Dx3 |
| | | 8 | mg/kg | PO | QDx5, rest for 3 cycles |
| | F-TdCyd | 200 | mg/kg | IV | Q7Dx3 |
| | 5-aza-T-dCyd | 1.5 | mg/kg | IP | QDx5 rest for 3 cycles |
| | gemcitabine | 150 | mg/kg | IP | Q7Dx3 |
| NCI-H23 | F-aza-TdCyd | 10 | mg/kg | IP | QDx5, rest for 3 cycles |
| NSCLC | | 80 | mg/kg | PO | QDx5, rest for 3 cycles |
| | | 400 | mg/kg | IP | Q7Dx3 |
| | F-TdCyd | 240 | mg/kg | IV | Q7Dx3 |
| | 5-aza-T-dCyd | 1.5 | mg/kg | IP | QDx5, rest for 3 cycles |
| | gemcitabine | 150 | mg/kg | IP | Q7Dx3 |
| HL-60 | F-aza-TdCyd | 10 | mg/kg | IP | QDx5, rest for 3 cycles |
| | | 400 | mg/kg | IP | Q7Dx3 |
| | F-TdCyd | 240 | mg/kg | IV | Q7Dx3 |
| | 5-aza-T-dCyd | 1.5 | mg/kg | IP | QDx5, rest for 3 cycles |
| | gemcitabine | 150 | mg/kg | IP | Q7Dx3 |

IP = intraperitonally,
IV = intravenously,
PO = orally
*Each cycle is one week. Thus, a "QDx5" cycle includes two days of rest.

Figure 12A:
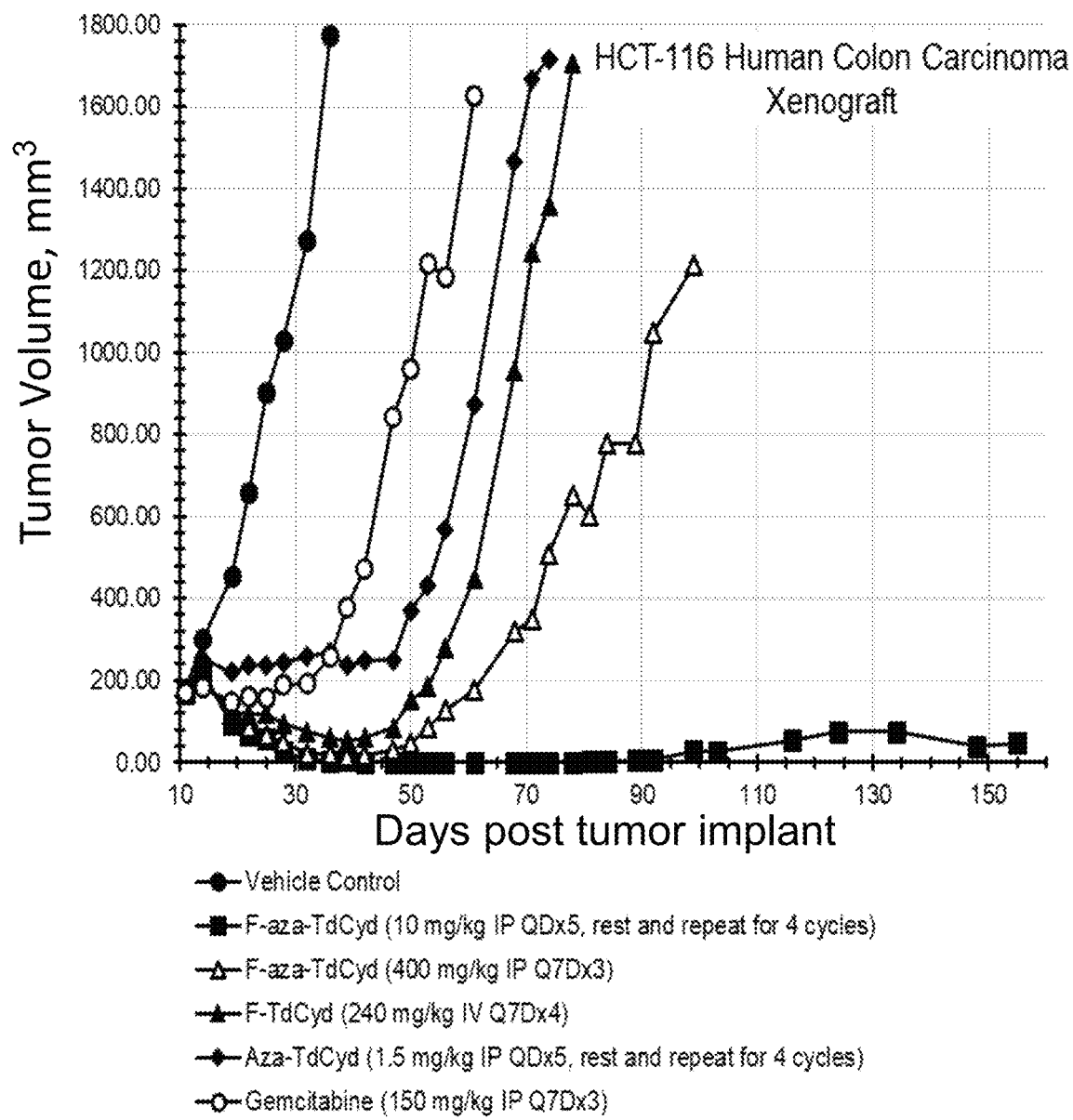
FIGS. 12A and 12B show HCT-116 human colon carcinoma xenograft tumor volume and mouse body weight, respectively, over time in mice administered 10 mg/kg Compound 1 (F-aza-TdCyd) intraperitoneally QDx5, rest and repeat for 4 cycles; 400 mg/kg Compound 1 intraperitoneally Q7Dx3; 240 mg/kg F-TdCyd intravenously Q7Dx4; 1.5 mg/kg 5-aza-T-dCyd intraperitoneally QDx5, rest and repeat for 4 cycles; or 150 mg/kg gemcitabine intraperitoneally Q7Dx3.
Figure 12B:
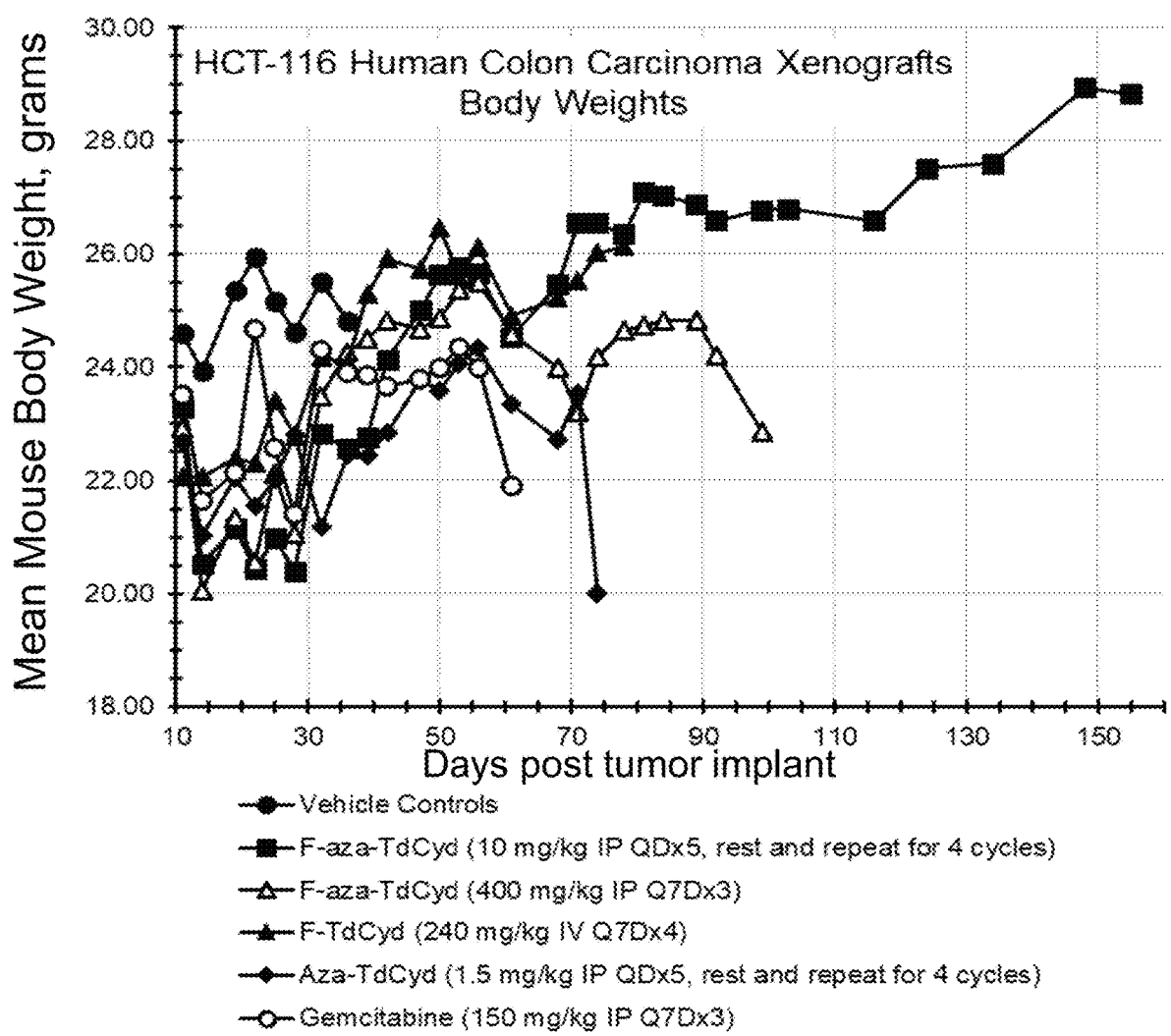
Figure 13A:
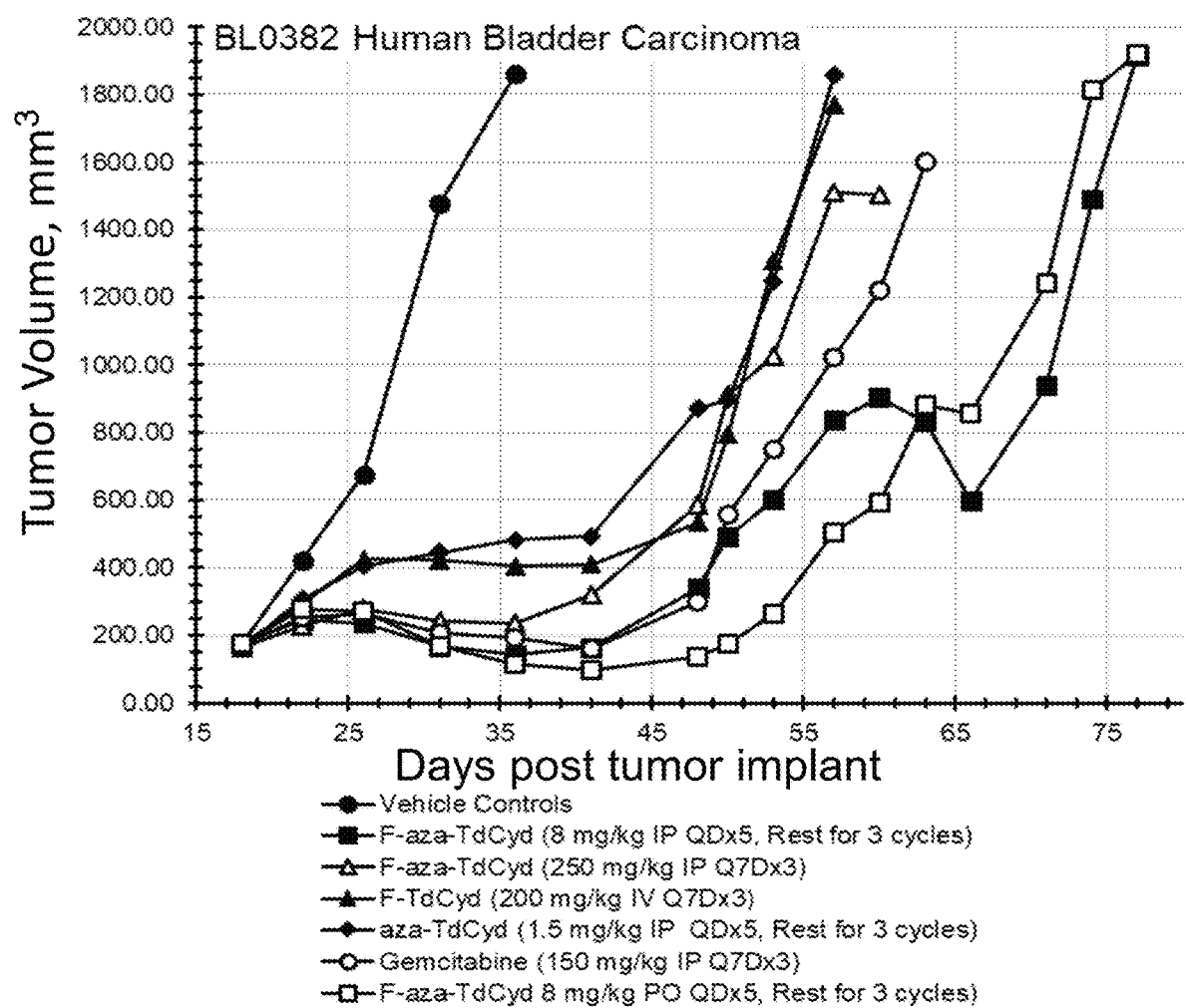
FIGS. 13A and 13B show BL0382 human bladder carcinoma xenograft tumor volume and mouse body weight, respectively, over time in mice administered 8 mg/kg Compound 1 (F-aza-TdCyd) intraperitoneally QDx5, rest for 3 cycles; 250 mg/kg Compound 1 intraperitoneally Q7Dx3; 200 mg/kg F-TdCyd intravenously Q7Dx3; 1.5 mg/kg 5-aza-T-dCyd intraperitoneally QDx5, rest and repeat for 3 cycles; 150 mg/kg gemcitabine intraperitoneally Q7Dx3; or 8 mg/kg Compound 1 orally QDx5, rest for 3 cycles.
Figure 13B:
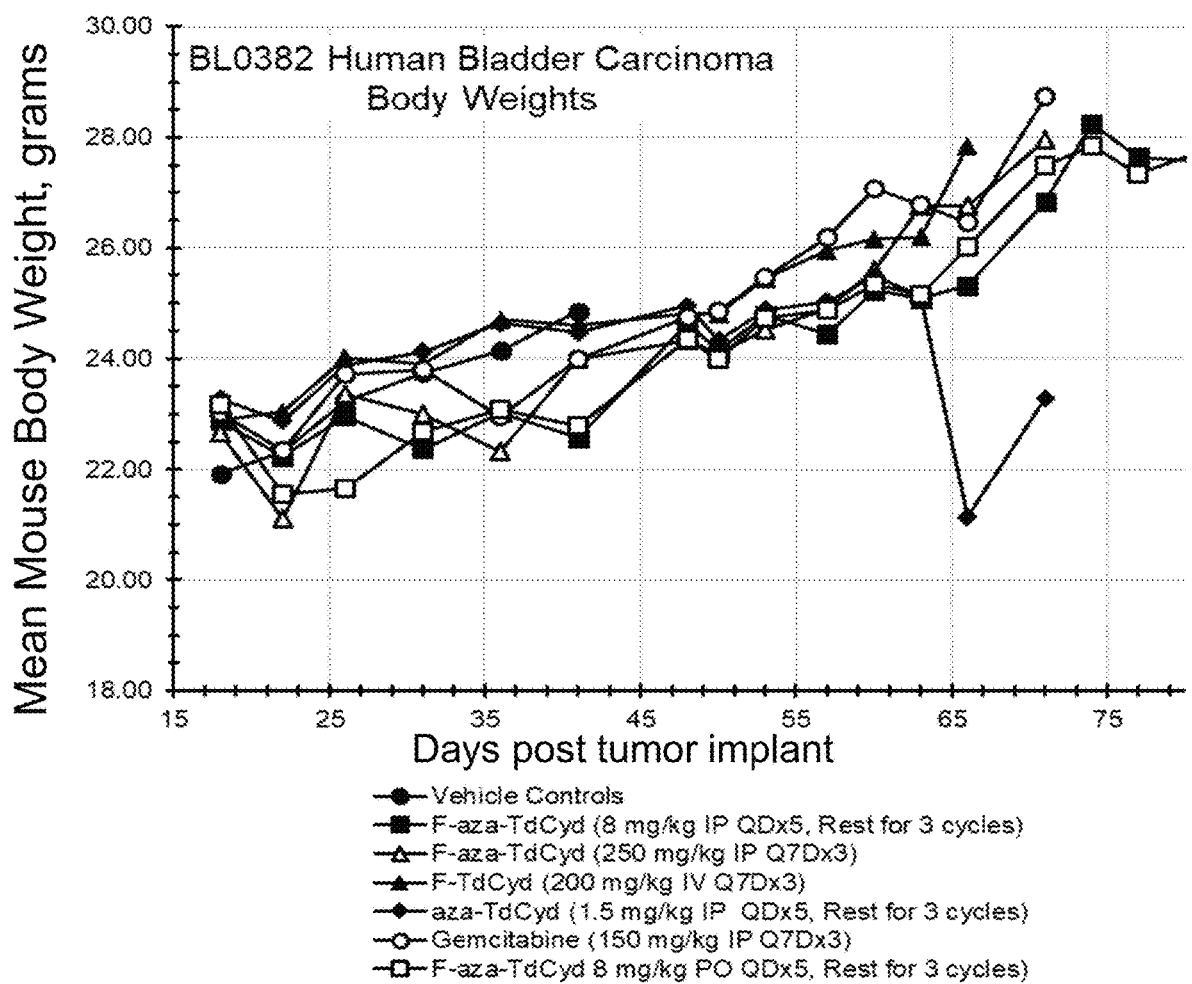
Figure 14A:
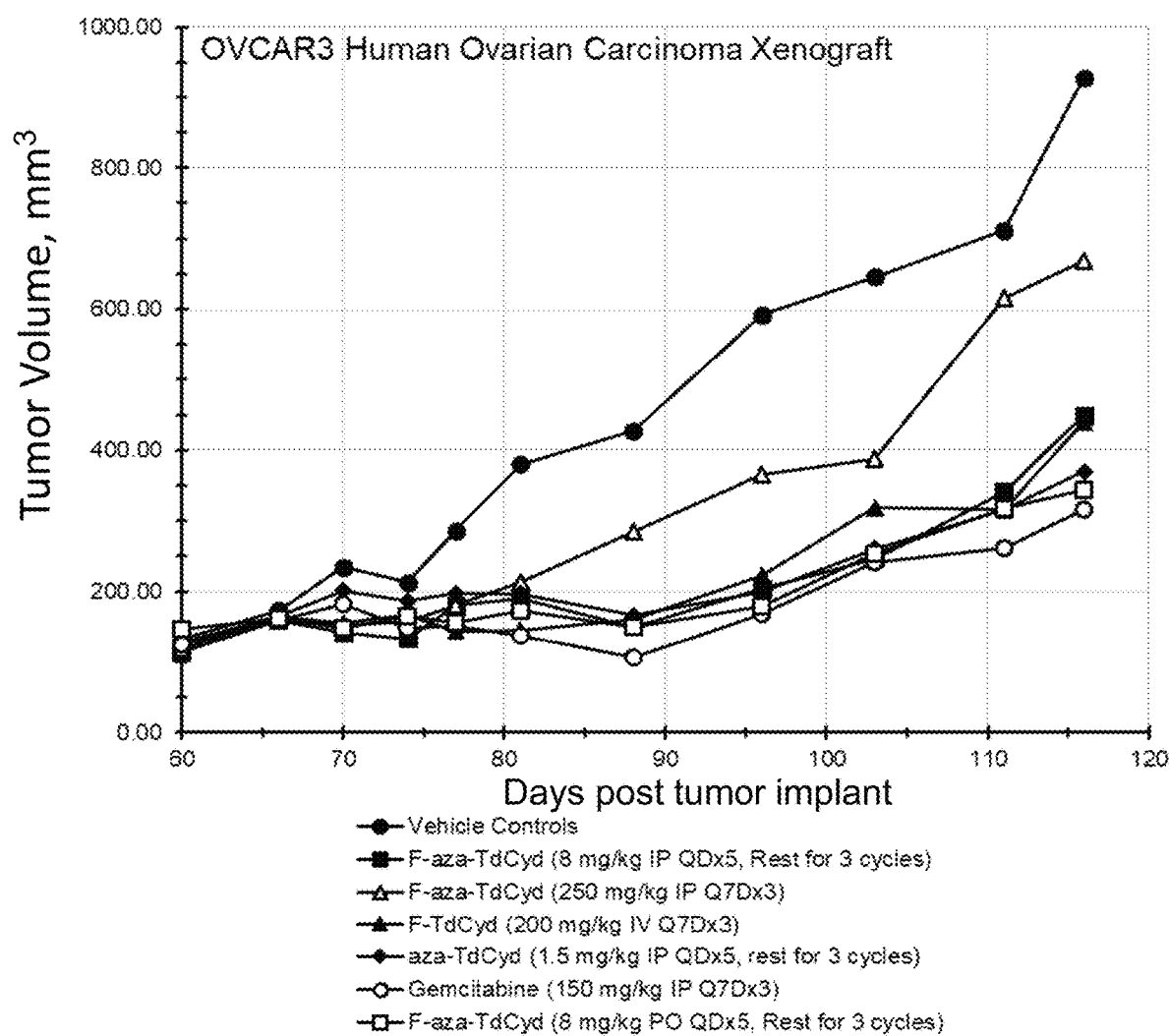
FIGS. 14A and 14B show OVCAR3 human ovarian carcinoma xenograft tumor volume and mouse body weight, respectively, over time in mice administered 8 mg/kg Compound 1 (F-aza-TdCyd) intraperitoneally QDx5, rest for 3 cycles; 250 mg/kg Compound 1 intraperitoneally Q7Dx3; 200 mg/kg F-TdCyd intravenously Q7Dx3; 1.5 mg/kg 5-aza-T-dCyd intraperitoneally QDx5, rest and repeat for 3 cycles; 150 mg/kg gemcitabine intraperitoneally Q7Dx3; or 8 mg/kg Compound 1 orally QDx5, rest for 3 cycles.
Figure 14B:
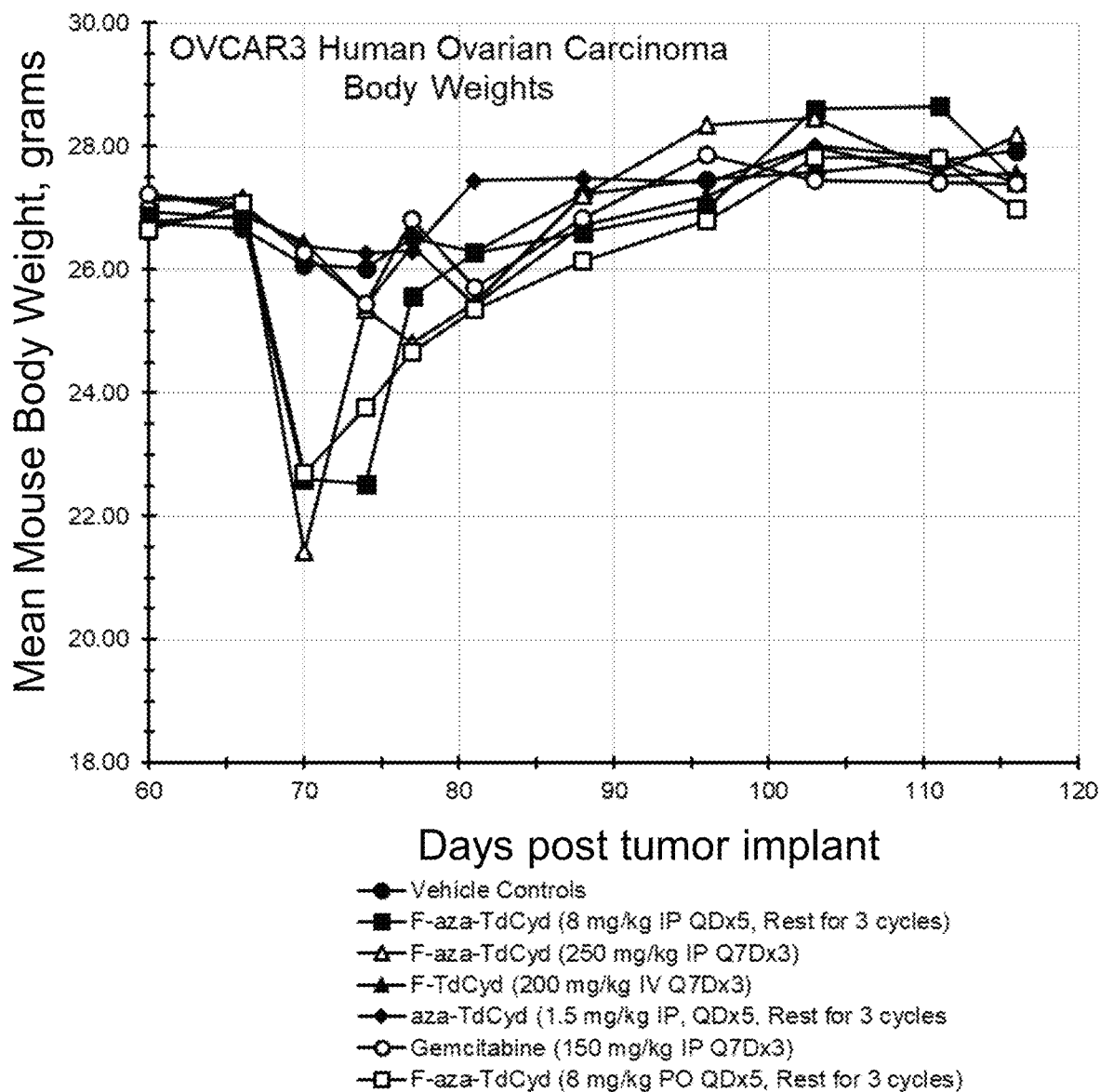
Figure 15A:
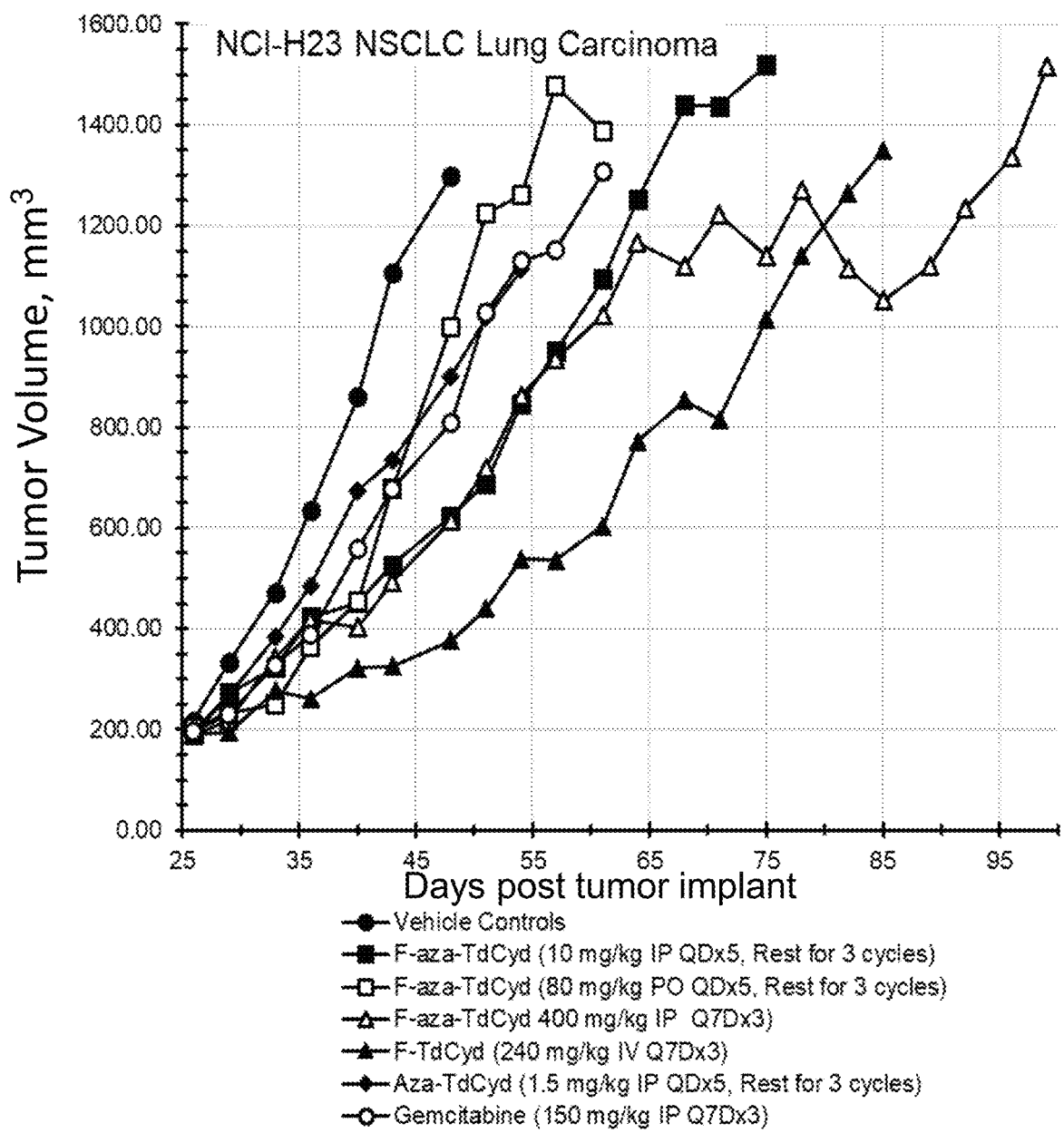
FIGS. 15A and 15B show NCI-H23 NSCLC human lung carcinoma xenograft tumor volume and mouse body weight, respectively, over time in mice administered 10 mg/kg Compound 1 (F-aza-TdCyd) intraperitoneally QDx5, rest for 3 cycles; 80 mg/kg Compound 1 orally QDx5, rest for 3 cycles; 400 mg/kg Compound 1 intraperitoneally Q7Dx3; 240 mg/kg F-TdCyd intravenously Q7Dx3; 1.5 mg/kg 5-aza-T-dCyd intraperitoneally QDx5, rest for 3 cycles; or 150 mg/kg gemcitabine intraperitoneally Q7Dx3.
Figure 15B:
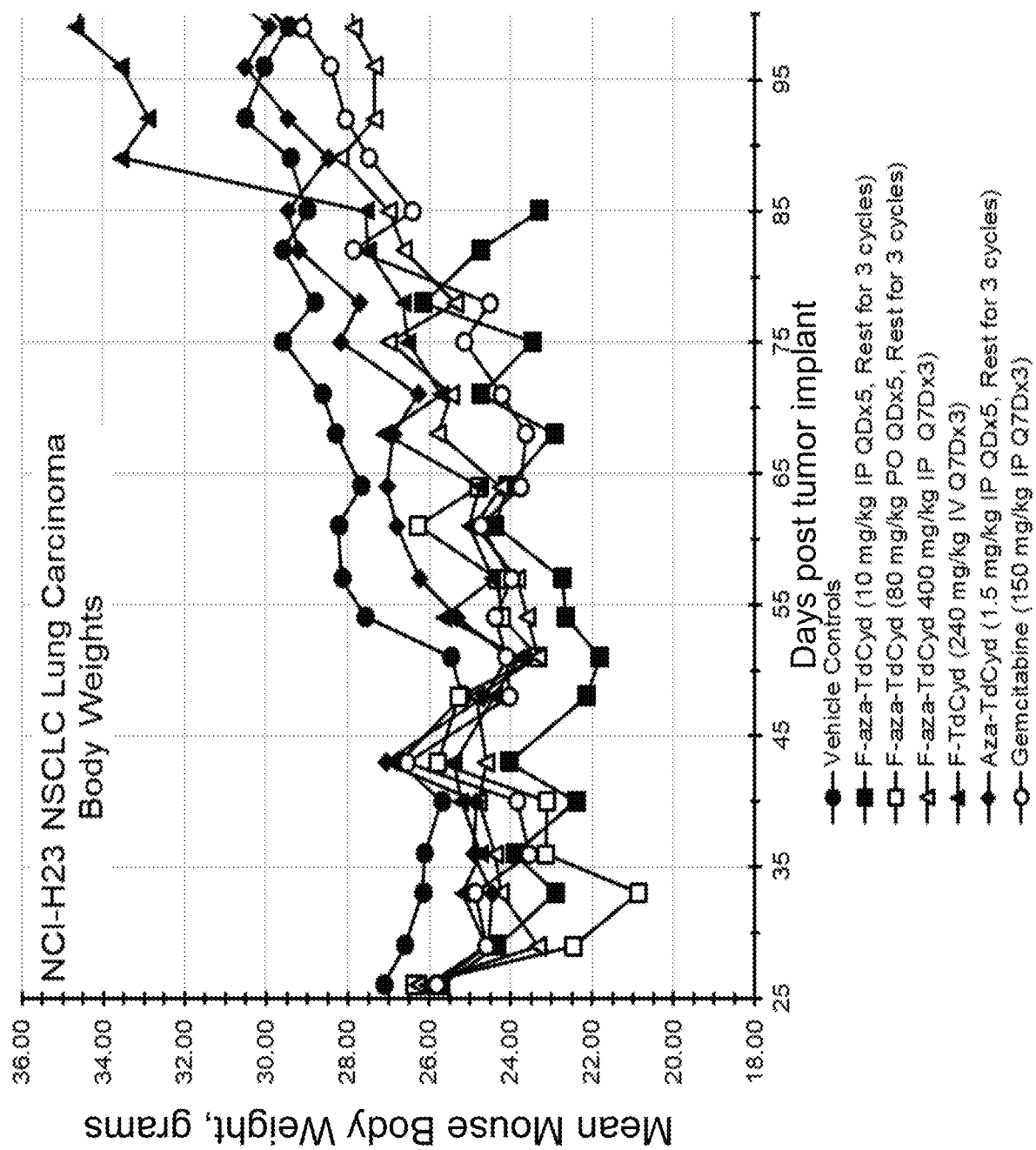
Figure 16A:
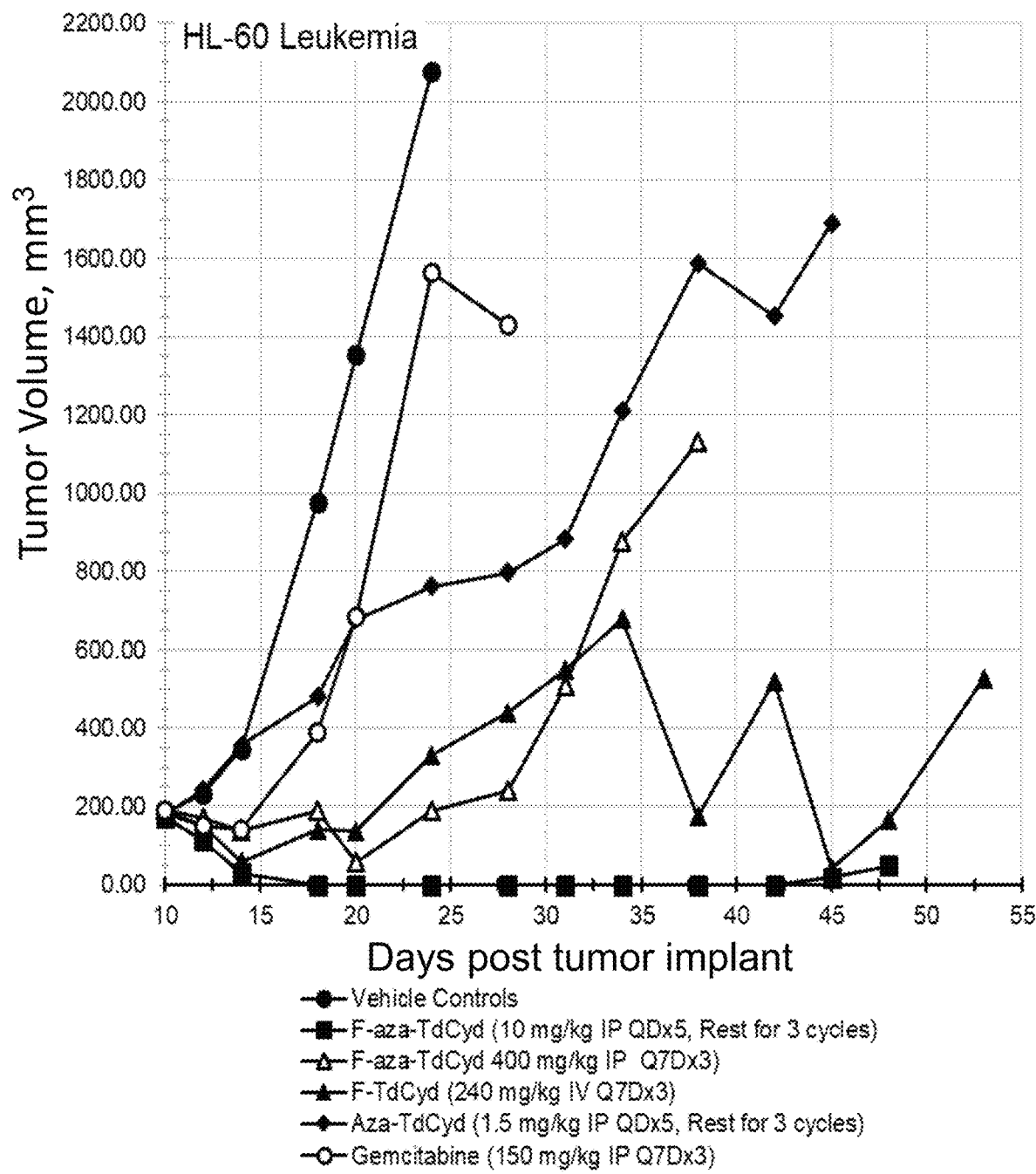
FIGS. 16A and 16B show HL-60 human leukemia xenograft tumor volume and mouse body weight, respectively, over time in mice administered 10 mg/kg Compound 1 (F-aza-TdCyd) intraperitoneally QDx5, rest for 3 cycles; 400 mg/kg Compound 1 intraperitoneally Q7Dx3; 240 mg/kg F-TdCyd intravenously Q7Dx3; 1.5 mg/kg 5-aza-T-dCyd intraperitoneally QDx5, rest for 3 cycles; or 150 mg/kg gemcitabine intraperitoneally Q7Dx3.
Figure 16B:
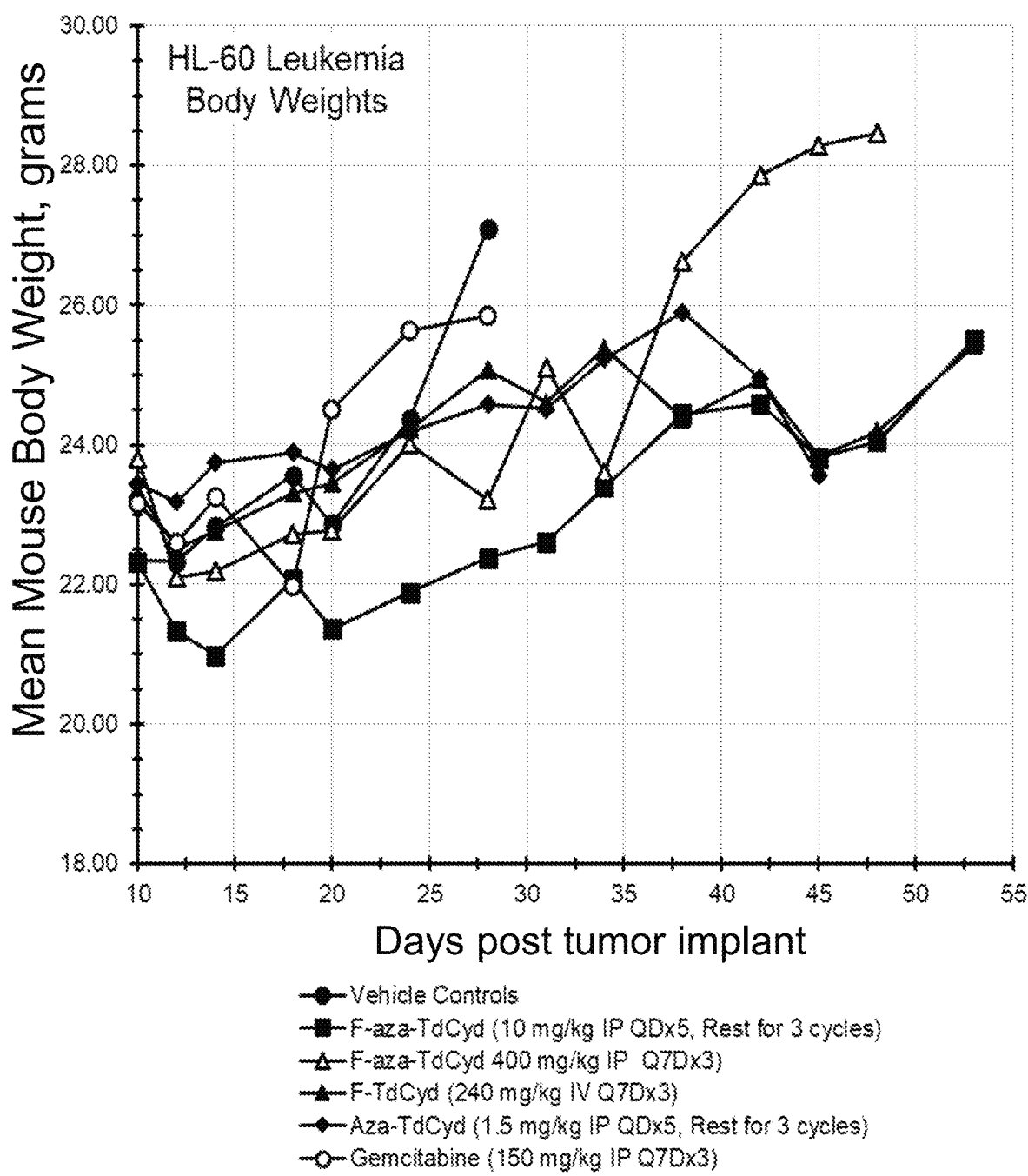

Serial measurements of tumor volume and body weight were obtained post tumor implant. The results are shown in FIGS. 12A and 12B (HCT-116 human colon carcinoma cells), 13A and 13B (BL0382 human bladder carcinoma cells), 14A and 14B (OVCAR3 human ovarian carcinoma cells), 15A and 15B (NCI-H23 NSCLC human lung carcinoma cells), and 16A and 16B (HL-60 human leukemia cells).

Example 4

Treatment with a Halogenated 5-Aza-T-dCyd Analog

A subject having, or suspected of having a disease, that may be treated with a halogenated 5-aza-T-dCyd analog is identified. The disease may be a disease characterized at least in part by the presence of neoplastic cells. In some instances, the disease is a cancer. The subject may be selected based on a clinical presentation and/or by performing tests to demonstrate presence of a disease, such as a cancer, characterized at least in part by presence of neoplastic cells. In some examples, the subject may have a solid tumor or a blood cancer.

The subject is treated by administering a halogenated 5-aza-T-dCyd analog, or a stereoisomer, tautomer, or pharmaceutically acceptable salt thereof at a dose determined by a clinician to be therapeutically effective. In some examples, the compound is 4-amino-1-((2R,3S,4S,5R)-3-fluoro-4-hydroxy-5-(hydroxymethyl)tetrahydrothiophen-2-yl)-1,3,5-triazin-2(1H)-one. The compound is administered by any suitable means, such as parenteral (e.g., intravenous, intraarterial, subcutaneous, intramuscular) or intrathecal injection or by oral administration. Treatment efficacy may be assessed by conventional means, e.g., prevention of tumor growth, reduction in tumor growth, reduction in or lack of metastasis, normalization of blood cell counts, and the like. In some examples, assessment is performed by computed tomography (CT), magnetic resonance imaging (MRI), or positron emission tomography (PET) scans.

A therapeutically effective amount of a second active agent may be co-administered with the compound. The compound and the second active agent may be administered either separately or together in a single composition. The second active agent may be administered by the same route or a different route. If administered concurrently, the compound and the second active agent may be combined in a single pharmaceutical composition or may be administered concurrently as two pharmaceutical compositions. The second active agent may be, for example, an anti-cancer agent, an anti-inflammatory agent, an antimicrobial agent, an antiviral agent, an anesthetic agent, or the like.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound, wherein the compound is 4-amino-1-((2R,3S,4S,5R)-3-fluoro-4-hydroxy-5-(hydroxymethyl)tetrahydrothiophen-2-yl)-1,3,5-triazin-2(1H)-one:

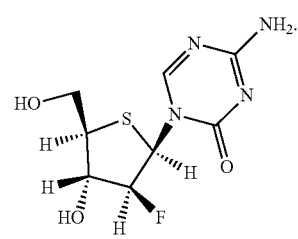 [SMILES: Nc1ncn([C@@H]2S[C@H](CO)[C@@H](O)[C@@H]2F)c(=O)n1]

2. A pharmaceutical composition comprising the compound of claim 1 and a pharmaceutically acceptable carrier.

* * * * *